US009896437B2

(12) United States Patent
Jung et al.

(10) Patent No.: US 9,896,437 B2
(45) Date of Patent: Feb. 20, 2018

(54) DIARYLHYDANTOIN COMPOUNDS

(71) Applicants: Michael E. Jung, Los Angeles, CA (US); Dongwon Yoo, Los Angeles, CA (US)

(72) Inventors: Michael E. Jung, Los Angeles, CA (US); Dongwon Yoo, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/224,005

(22) Filed: Mar. 24, 2014

(65) Prior Publication Data

US 2015/0065546 A1    Mar. 5, 2015

Related U.S. Application Data

(62) Division of application No. 12/257,743, filed on Oct. 24, 2008, now Pat. No. 8,680,291.

(60) Provisional application No. 60/996,076, filed on Oct. 26, 2007.

(51) Int. Cl.
| | |
|---|---|
| A61K 31/4166 | (2006.01) |
| A61K 31/4178 | (2006.01) |
| A61K 31/4184 | (2006.01) |
| C07D 403/10 | (2006.01) |
| C07D 233/86 | (2006.01) |
| C07D 235/02 | (2006.01) |

(52) U.S. Cl.
CPC ........ *C07D 403/10* (2013.01); *A61K 31/4166* (2013.01); *A61K 31/4178* (2013.01); *A61K 31/4184* (2013.01); *C07D 233/86* (2013.01); *C07D 235/02* (2013.01)

(58) Field of Classification Search
CPC ............ A61K 31/4166; A61K 31/4178; A61K 31/4184
USPC ............................ 548/301.4, 316.7; 514/391
See application file for complete search history.

(56) References Cited

U.S. PATENT DOCUMENTS

| | | | |
|---|---|---|---|
| 3,823,240 A | 7/1974 | Sauli | |
| 3,923,994 A | 12/1975 | Magnani | |
| 3,970,662 A | 7/1976 | Carabateas et al. | |
| 3,984,430 A | 10/1976 | Curran | |
| 4,097,578 A | 6/1978 | Perronnet et al. | |
| 4,234,736 A | 11/1980 | Bernauer et al. | |
| 4,304,782 A | 12/1981 | Dumont et al. | |
| 4,312,881 A | 1/1982 | Wootton | |
| 4,386,080 A | 5/1983 | Crossley et al. | |
| 4,399,216 A | 8/1983 | Axel et al. | |
| 4,407,814 A | 10/1983 | Bernauer et al. | |
| 4,427,438 A | 1/1984 | Nagano et al. | |
| 4,432,987 A | 2/1984 | Barth et al. | |
| 4,473,393 A | 9/1984 | Nagpal | |
| 4,482,739 A | 11/1984 | Bernauer et al. | |
| 4,559,157 A | 12/1985 | Smith et al. | |
| 4,608,392 A | 8/1986 | Jacquet et al. | |
| 4,636,505 A | 1/1987 | Tucker | |
| 4,749,403 A | 6/1988 | Liebl et al. | |
| 4,753,957 A | 6/1988 | Chan | |
| 4,820,508 A | 4/1989 | Wortzman | |
| 4,859,228 A | 8/1989 | Prisbylla | |
| 4,873,256 A | 10/1989 | Coussediere et al. | |
| 4,938,949 A | 7/1990 | Borch et al. | |
| 4,944,791 A | 7/1990 | Schroder et al. | |
| 4,992,478 A | 2/1991 | Geria | |
| 5,010,182 A | 4/1991 | Brake et al. | |
| 5,069,711 A | 12/1991 | Fischer et al. | |
| 5,071,773 A | 12/1991 | Evans et al. | |
| 5,084,472 A | 1/1992 | Moguilewsky et al. | |
| 5,166,358 A | 11/1992 | Seuron et al. | |
| 5,411,981 A | 5/1995 | Gaillard-Kelly et al. | |
| 5,434,176 A | 7/1995 | Claussner et al. | |
| 5,554,607 A | 9/1996 | Elokdah et al. | |
| 5,556,983 A | 9/1996 | Claussner et al. | |
| 5,589,497 A | 12/1996 | Claussner et al. | |
| 5,614,620 A | 3/1997 | Liao et al. | |
| 5,627,201 A | 5/1997 | Gaillard-Kelly et al. | |
| 5,646,172 A | 7/1997 | Claussner et al. | |
| 5,656,651 A | 8/1997 | Sovak et al. | |
| 5,705,654 A | 1/1998 | Claussner et al. | |
| 5,726,061 A | 3/1998 | Robbins et al. | |
| 5,750,553 A | 5/1998 | Claussner et al. | |
| 5,783,707 A | 7/1998 | Elokdah et al. | |
| RE35,956 E | 11/1998 | Gaillard-Kelly et al. | |
| 5,958,936 A | 9/1999 | Claussner et al. | |
| 5,985,868 A | 11/1999 | Gray | |
| 6,087,509 A | 7/2000 | Claussner et al. | |
| 6,107,488 A | 8/2000 | Bouchet et al. | |
| 6,107,957 A | 8/2000 | Cramer et al. | |

(Continued)

FOREIGN PATENT DOCUMENTS

| | | |
|---|---|---|
| AU | 217893 | 6/1958 |
| AU | 2005280908 A1 | 3/2006 |

(Continued)

OTHER PUBLICATIONS

Golub et al., Science, vol. 286, Oct. 15, 1999, pp. 531-537.*
U.S. Appl. No. 60/680,835, filed May 13, 2005, Sawyers et al.
U.S. Appl. No. 60/750,351, filed Dec. 15, 2005, Jung et al.
U.S. Appl. No. 60/756,552, filed Jan. 6, 2006, Jung et al.
A Textbook of Drug Design and Development, P. Krogsgaard-Larson and H. Bundgaard, eds. Ch 5, pp. 113-191 (Harwood Academic Publishers, 1991).
A.M. Soto et al. Control of Cell Proliferation: Evidence for Negative Control on Estrogen-sensitive T47D Human Breast Cancer Cells:, Cancer Research, 46, (1986), pp. 2271-2275.

(Continued)

*Primary Examiner* — Laura L. Stockton
(74) *Attorney, Agent, or Firm* — Venable LLP; Lars H. Genieser; Keith G. Haddaway

(57) ABSTRACT

The present invention relates to diarylhydantoin compounds and methods for synthesizing them and using them in the treatment of hormone refractory prostate cancer.

21 Claims, No Drawings

(56) References Cited

U.S. PATENT DOCUMENTS

| | | |
|---|---|---|
| 6,172,076 B1 | 1/2001 | Embrey et al. |
| 6,184,249 B1 | 2/2001 | Sovak et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,518,257 B1 | 2/2003 | Tasaka et al. |
| 6,828,471 B2 | 12/2004 | Sawyers et al. |
| 6,949,521 B2 | 9/2005 | Chu et al. |
| 7,067,537 B2 | 6/2006 | Kuroda et al. |
| 7,138,421 B2 | 11/2006 | Cleve et al. |
| 7,205,437 B2 | 4/2007 | Dalton et al. |
| 7,241,769 B2 | 7/2007 | Stadtmueller et al. |
| 7,271,188 B2 | 9/2007 | Tachibana et al. |
| 7,601,748 B2 | 10/2009 | Cleve et al. |
| 7,709,517 B2 | 5/2010 | Sawyers et al. |
| 7,718,684 B2 | 5/2010 | Jung et al. |
| 8,034,548 B2 | 10/2011 | Sawyers et al. |
| 8,110,594 B2 | 2/2012 | Jung et al. |
| 8,183,274 B2 | 5/2012 | Sawyers et al. |
| 8,445,507 B2 | 5/2013 | Jung et al. |
| 8,648,105 B2 | 2/2014 | Jung et al. |
| 8,680,291 B2 | 3/2014 | Jung et al. |
| 8,802,689 B2 | 8/2014 | Jung et al. |
| 9,126,941 B2 | 9/2015 | Sawyers et al. |
| 9,388,159 B2 | 7/2016 | Jung et al. |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/1002992 | 2/2004 | Kuduk et al. |
| 2004/0116417 A1 | 6/2004 | Boubia et al. |
| 2005/0153968 A1 | 7/2005 | Bi et al. |
| 2005/0154028 A1 | 7/2005 | Bromidge et al. |
| 2006/0127902 A1 | 6/2006 | Madden et al. |
| 2007/0004753 A1 | 1/2007 | Sawyers et al. |
| 2007/0135492 A1 | 6/2007 | Lange et al. |
| 2007/0166717 A1 | 7/2007 | Sawyer et al. |
| 2007/0249697 A1 | 10/2007 | Tachibana et al. |
| 2007/0254933 A1 | 11/2007 | Jung et al. |
| 2008/0139634 A2 | 6/2008 | Jung et al. |
| 2009/0111864 A1 | 4/2009 | Jung et al. |
| 2010/0172975 A1 | 7/2010 | Sawyers et al. |
| 2010/0210665 A1 | 8/2010 | Sawyers et al. |
| 2011/0003839 A1 | 1/2011 | Jung et al. |
| 2011/0130296 A1 | 6/2011 | Benz et al. |
| 2011/0152348 A1 | 6/2011 | Worm et al. |
| 2012/0214864 A1 | 8/2012 | Richer et al. |
| 2013/0190507 A1 | 7/2013 | Jain et al. |
| 2015/0112082 A1 | 4/2015 | Sawyers et al. |
| 2017/0014399 A1 | 1/2017 | Jung et al. |

FOREIGN PATENT DOCUMENTS

| | | |
|---|---|---|
| CN | 101032483 A | 9/2007 |
| DE | 2102605 A1 | 7/1971 |
| DE | 2126187 A1 | 12/1971 |
| DE | 2614831 A1 | 10/1977 |
| EP | 0 001 813 A1 | 5/1979 |
| EP | 0017976 B1 | 10/1980 |
| EP | 0 091 596 A2 | 10/1983 |
| EP | 0002259 B1 | 10/1984 |
| EP | 0144098 A1 | 6/1985 |
| EP | 0331232 A2 | 9/1989 |
| EP | 362179 A2 | 4/1990 |
| EP | 0 436 426 A1 | 7/1991 |
| EP | 0572191 A1 | 12/1993 |
| EP | 0578516 A1 | 1/1994 |
| EP | 0580459 A1 | 1/1994 |
| EP | 0494819 A1 | 7/1996 |
| EP | 0494819 B1 | 7/1996 |
| EP | 0721944 B1 | 7/1996 |
| EP | 0770613 A1 | 5/1997 |
| EP | 1790640 A1 | 5/2007 |
| EP | 2400847 | 1/2012 |
| FR | 2 075 751 A5 | 10/1971 |
| FR | 2 329 276 A1 | 5/1977 |
| FR | 2693461 A1 | 1/1994 |
| FR | 2715402 A1 | 7/1995 |
| FR | 2845384 A1 | 4/2004 |
| GB | 2175903 A | 12/1986 |
| JP | 48087030 U | 10/1973 |
| JP | 59210083 A | 11/1984 |
| JP | 1009978 A | 1/1989 |
| JP | 2019363 A | 1/1990 |
| JP | 6-073017 A | 3/1994 |
| JP | 10-510845 A | 10/1998 |
| JP | 38045455 B2 | 11/2006 |
| JP | 2009-531449 A | 9/2009 |
| RU | 2116298 C1 | 7/1998 |
| RU | 2152934 C1 | 7/2000 |
| WO | WO-9013646 A1 | 11/1990 |
| WO | WO-9518794 A1 | 7/1995 |
| WO | WO-9700071 A1 | 1/1997 |
| WO | WO-9719064 A1 | 5/1997 |
| WO | WO-9719931 A1 | 6/1997 |
| WO | WO-0017163 A1 | 3/2000 |
| WO | WO-0026195 A1 | 5/2000 |
| WO | WO-0044731 A1 | 8/2000 |
| WO | WO-0107048 A1 | 2/2001 |
| WO | WO-0192253 A2 | 12/2001 |
| WO | WO-0194346 A1 | 12/2001 |
| WO | WO-0242488 A1 | 5/2002 |
| WO | WO2002/046186 A1 | 6/2002 |
| WO | WO-02053155 A1 | 7/2002 |
| WO | WO-02081453 A1 | 10/2002 |
| WO | WO-03029245 A1 | 4/2003 |
| WO | WO-03032994 A2 | 4/2003 |
| WO | WO-03057220 A1 | 7/2003 |
| WO | WO2003/065789 A2 | 8/2003 |
| WO | WO-03093243 A1 | 11/2003 |
| WO | WO-03096980 A2 | 11/2003 |
| WO | WO2004/001059 A2 | 12/2003 |
| WO | WO-2004022572 A1 | 3/2004 |
| WO | WO-2004031160 A2 | 4/2004 |
| WO | WO-2004070050 A2 | 8/2004 |
| WO | WO-2004111031 A1 | 12/2004 |
| WO | WO2005/037797 A1 | 4/2005 |
| WO | WO-2005042488 A1 | 5/2005 |
| WO | WO 2005/049580 A1 | 6/2005 |
| WO | WO-2005059109 A2 | 6/2005 |
| WO | WO-2005060661 A2 | 7/2005 |
| WO | WO-2005089752 A2 | 9/2005 |
| WO | WO-2005099693 A2 | 10/2005 |
| WO | WO-2006010642 A1 | 2/2006 |
| WO | WO-2006028226 A1 | 3/2006 |
| WO | WO-2006124118 A1 | 11/2006 |
| WO | WO-2007045877 A1 | 4/2007 |
| WO | WO-2007126765 A2 | 11/2007 |
| WO | WO-2007127010 A2 | 11/2007 |
| WO | WO-2008119015 A2 | 10/2008 |
| WO | WO-2009055053 A2 | 4/2009 |
| WO | WO-2009076408 A2 | 6/2009 |
| WO | WO-2010/099238 A1 | 9/2010 |
| WO | WO2010/099238 A1 | 9/2010 |
| WO | WO2010/118354 A1 | 10/2010 |
| WO | WO2011/044327 A1 | 4/2011 |

OTHER PUBLICATIONS

Abrahamsson P. et al., "Risks and Benefits of Hormonal Manipulation as Monotherapy or Adjuvant Treatment in Localised Prostate Cancer," 2005 European Urology vol. 45, pp. 900-905.

Abstract submitted by Samedy Ouk, Prostate Cancer Foundation Scientific Retreat, Scottsdale, Arizona, Sep. 29-Oct. 1, 2005.

Aly et al., "Functionality of amidines and amidrazones," ARKIVOC (i), pp. 153-194 (2008).

Ametamey et al., "Reaktionen von 3-(Dimethylamino)-2H-azirinen mit 1,3-Benzoxazol-2(3H)-thion," Helvetica Chima Acta, vol. 73, No. 3, pp. 599-607 & title page (1990).

(56) References Cited

OTHER PUBLICATIONS

Ausubel et al., Current Protocols in Molecular Biology, Wiley Interscience Publishers, (1995).
Baek, S.H. et al. Exchange of N-CoR corepressor and Tip60 coactivator complexes links gene expression by NF-kappaB and beta-amyloid precursor protein. Cell 110, 55-67 (2002).
Balk, S.P. Androgen receptor as a target in androgen-independent prostate cancer. Urology 60, 132-8; discussion 138-9 (2002).
Batch,J.A., et al., "Androgen receptor gene mutations identified by SSCP in fourteen subjects with androgen insensitivity syndrome", Hum. Mol. Genet. 1 (7), 497-503 (1992).
Bohl et al., "Structural basis for antagonism and resistance of bicalutamide in prostate cancer", Proc. Nat. Acad. Sci., 2005, v. 102(17), pp. 6201-6206.
Brockschmidt,F.F., et al., "The two most common alleles of the coding GGN repeat in the androgen receptor gene cause differences in protein function", J. Mol. Endocrinol. 39 (1), 1-8 (2007).
Burnstein et al. Androgen Glucocorticoid Regulation of Androgen Receptor cDNA Expression. Molecular and Cellular Endocrinology. 1995. v. 115, pp. 177-186.
Cai,C., et al., "c-Jun has multiple enhancing activities in the novel cross talk between the androgen receptor and Ets variant gene 1 in prostate cancer", Mol. Cancer Res. 5 (7), 725-735 (2007).
Chang et al., "Molecular cloning of human and rate complementary DNA encoding androgen receptors," Science 240 (4850), 324-326 (1988).
Chemical Abstracts Search provided with Oct. 8, 2010 Office Action in U.S. Appl. No. 11/730,168.
Chemical Abstracts, vol. 114, p. 185368 (May 13, 1991).
Chen, C.D. et al., "Molecular determinants of resistance to antiandrogen therapy", Nature Medicine, vol. 10, No. 1 (Jan. 2004) pp. 33-39.
Cinar et al. Androgen Receptor Mediates the Reduced Tumor Growth, Enhanced Androgen Responsiveness, and Selected Target Gene Transactivation in Human Prostate Cancer Cell Line. Cancer Research. 2001. v. 61. pp. 7310-7317.
Clegg et al., "ARN-509: A Novel Antiandrogen for Prostate Cancer Treatment," Cancer Res. 2012; 72:1494-1503.
Corrected Notice of Allowability issued in U.S. Appl. No. 11/730,168 mailed Jan. 19, 2012.
Corrected Notice of Allowability issued in U.S. Appl. No. 11/730,168 mailed Dec. 22, 2011.
Cousty-Berlin, et al., "Preliminary Pharmacokinetics and Metabolism of Novel Non-steroidal Antiandrogens in the Rat: Relation of their Systemic Activity to the Formation of a Common Metabolite," J. Steroid Biochem. Molec. Biol., vol. 51, No. 1/2, pp. 47-55 (1994).
Craft, N. et al. Evidence for clonal outgrowth of androgen-independent prostate cancer cells from androgen-dependent tumors through a two-step process. Cancer Res 59,5030-6 (1999).
Craft, N., Shostak, Y., Carey, M. & Sawyers, C.L. A mechanism for hormone-independent prostate cancer through modulation of androgen receptor signaling by the HER-2/neu tyrosine kinase. Nat Med 5, 280-5 (1999).
Creaven, P.J. et al., "Pharmacokinetics and Metabolism of Nilutamide", Supp. Urology, vol. 37, No. 2 (Feb. 1991) pp. 13-19.
Crooks et al., "The Structure of Some Reaction Products of 2,3-Dihydrophenalene-1,2,3-Trione with Urea and its Homologues," Gazzetta Chimica Italiana, vol. 107, No. 5-6, pp. 353-354 & title page (1977).
Data Sheet from U.S. Appl. No. 08/807,760 (1998).
Database CA Chemical Abstracts Service, Columbus, Ohio, US; Jan. 1, 1994. Dhal, P. N. et al. Synthesis of thiohydantoins, thiazolidones, and their derivatives from N1-(4'-arylthiazol-2'-yl)thioureas. J Ind Chem Soc. 50:680-684. 1973.
Database CA, Chemical Abstracts Service (1994), Dhal P.N., J Indian Chem Soc 50 (1973) 680-684.
DePrimo, S.E. et al. Transcriptional programs activated by exposure of human prostate cancer cells to androgen. Genome Biol 3, RESEARCH0032 (2002).

Design of Prodrugs, edited by H. Bundgaard, (Elsevier, 1985).
Dhal et al., "Synthesis of Thiohydantoins, Thiazolidones and Their Derivatives from N-(4'-Aryl Thiazole 2'-YL) Thioureas," J. Indian Chem. Soc., vol. L, pp. 680-684 (Oct. 1973).
Dyer et al., "Preparation of Polyhydrouracils and Polyiminoimidazolidinones," Journal of Polymer Science, Part A-1, vol. 7, pp. 833-849 & title page (1969).
Edwards, J., Krishna, N.S., Grigor, K.M. & Bartlett, J.M. Androgen receptor gene amplification and protein expression in hormone refractory prostate cancer. Br J Cancer 89, 552-6 (2003).
Ellis, W.J. et al. Characterization of a novel androgen-sensitive, prostate-specific antigen-producing prostatic carcinoma xenograft: LuCaP 23. Clin Cancer Res 2, 1039-48 (1996).
Ellwood-Yen, K. et al. Myc-driven murine prostate cancer shares molecular features with human prostate tumors. Cancer Cell 4, 223-38 (2003).
Espada et al., "N3-Arylspiroimidazolidine-2,4-Diones, N3-Arylspiroimidazolidine-2-Thio-4-ones and 4-Hydroxy Derivatives. Synthesis and Anthelminitic Activity," Il Farmaco, vol. 45, No. 11, pp. 1237-1243 & title page (1990).
European Office Action issued in European Application No. 11 178 889.9 dated Aug. 29, 2012.
European Search Report dated Jul. 20, 2011 for European Application No. 07754060.7, 7 pages.
European Search Report issued in Application No. 12193684.3 dated Jan. 22, 2013.
European Search Report issued in European Application No. 80102042 (1981).
European Search Report issued in European Application No. 06748863.5, mailed on Feb. 12, 2009.
European Search Report dated Aug. 8, 2011 (search completed Jul. 12, 2011) for European Application No. 11163948.0, 10 pages.
Feher, et al., "BHB: A Simple Knowledge-Based Scoring Function to Improve the Efficiency of Database Screening," J. Chem. Inf. Comput. Sci., vol. 43, pp. 1316-1327 (2003).
Feldman, B.J. & Feldman, D. The development of androgen-independent prostate cancer. Nat Rev Cancer 1, 34-45 (2001).
Final Office Action in U.S. Appl. No. 12/708,523 mailed on May 5, 2011.
Font de Mora, J. & Brown, M. AIB1 is a conduit for kinase-mediated growth factor signaling to the estrogen receptor. Mol Cell Biol 20, 5041-7 (2000).
Foury, et al., "Control of the Proliferation of Prostate Cancer Cells by an Androgen and Two Antiandrogens. Cell Specific Sets of Responses," J. Steroid Biochem. Molec. Biol., vol. 66, No. 4, pp. 235-240 (1998).
Gelmann, E.P. Molecular biology of the androgen receptor. J Clin Oncol 20, 3001-15 (2002).
Gioeli, D. et al. Androgen receptor phosphorylation. Regulation and identification of the phosphorylation sites. J Biol Chem 277, 29304-14 (2002).
Glass, C.K. & Rosenfeld, M.G. The coregulator exchange in transcriptional functions of nuclear receptors. Genes Dev 14, 121-41 (2000).
Goubet, et al., Conversion of a Thiohydantoin to the Corresponding Hydantoin via a Ring-Opening/Ring Closure Mechanism, *Tetrahedron Letters*, vol. 37, No. 43, pp. 7727-7730 (1996).
Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).
Graham and van der Eb, "A new technique for the assay of infectivity of human adenovirus 5 DNA", Virology, v. 52(2) (Apr. 1973) pp. 456-467.
Gregory, C.W. et al. A mechanism for androgen receptor-mediated prostate cancer recurrence after androgen deprivation therapy. Cancer Res 61, 4315-9 (2001).
Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8. (2001).

(56) References Cited

OTHER PUBLICATIONS

Günzl et al., "Zur Chemie der vicinalen Triketone, XIII, Versuche zur Darstellung von Schiffschen Basen aus cyclischen, vicinalen Triketonen," Monatshefte für Chemie, vol. 113, No. 11, pp. 1299-1310 & title page (1982).
Hamilton-Reeves,J.M., et al., "Isoflavone-rich soy protein isolate suppresses androgen receptor expression without altering estrogen receptor-beta expression or serum hormonal profiles in men at high risk of prostate cancer", J. Nutr. 137 (7), 1769-1775 (2007).
Hassan et al. Design, synthesis, and biological evaluation of thio-containing compounds with serum HDL-cholesterol-elevating properties. J Med Chem. 2004 47(29): 681-695.
Holzbeierlein, J. et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.
Homma,S., et al., "Differential levels of human leukocyte antigen-class I, multidrug-resistance 1 and androgen receptor expressions in untreated prostate cancer cells: the robustness of prostate cancer", Oncol. Rep. 18 (2), 343-346 (2007).
Hoerig et al. From bench to clinic and back: Perspective on 1st IQPC Translational Research Conference. 2004. Journal of Translational Medicine. 2:44.
Horoszewicz, J.S. et al. LNCaP model of human prostatic carcinoma. Cancer Res 43, 1809-18 (1983).
Examination Report issued in Australian Application No. 2007245022 dated Nov. 12, 2012.
Examination Report issued in New Zealand Application No. 601503 dated Jul. 31, 2012.
Statement by Applicant of Mar. 21, 2013 (incorporated into filed IDS Transmittal Letter.
International Search Report issued in International Application No. PCT/US2004/042258 dated Aug. 7, 2006.
European Search Report issued in European Application No. 83103022, dated Nov. 21, 1984.
Hough, "Synthesis of Imidazolin-2-ones by Rearrangement of N-Carbamoyliminium Salts Derived From 4-Hydroxyimidazolidin-2-ones," Journal of Heterocyclic Chemistry, vol. 26, No. 6, pp. 1523-1525 & title page (1989).
Huang, Z.Q., Li, J. & Wong, J. AR possess an intrinsic hormone-independent transcriptional activity. Mol Endocrinol 16, 924-37 (2002).
International Search Report issued in International Application No. PCT/US2007/007854, mailed on Apr. 15, 2008.
International Search Report issued in International Application No. PCT/US2008/012149 mailed on Apr. 29, 2009.
International Search Report issued in PCT Application No. PCT/US06/11417 dated Jul. 3, 2006.
International Search Report issued in PCT Application No. PCT/US2003/015375, mailed Dec. 3, 2003.
International Search Report issued in PCT Application PCT/US2004/042221, mailed on Jun. 20, 2005.
International Search Report issued in PCT Application PCT/US2005/005529, mailed on Nov. 10, 2005.
International Search Report issued in PCT Application PCT/US2007/07485, mailed on Sep. 4, 2008.
International Search Report issued in PCT Application PCT/US96/10286 (1996).
Jones, "Proteinase Mutants of *Saccharomyces cerevisiae*," Genetics, 85: 23-33 (1977).
Jung et al. Structure-Activity Relationship for Thiohydantoin Androgen Receptor Antagonists for Castration-Resistant Prostate Cancer (CRPC). 2010. J Med Chem. 53:2779-2796.
Karp et al., "Prostate Cancer Prevention: Investigational Approaches and Opportunities", Cancer Res., v. 56 (Dec. 15, 1996) pp. 5547-5556.
Karvonen, et al., "Interaction of Androgen Receptors with Androgen Response Element in Intact Cells," The Journal of Biological Chemistry, vol. 272, No. 25, pp. 15973-15979 (1997).

Kato, S. et al. Activation of the estrogen receptor through phosphorylation by mitogen-activated protein kinase. Science 270, 1491-4 (1995).
Kemppainen, et al., "Distinguishing Androgen Receptor Agonists and Antagonists: Distinct Mechanisms of Activation by Medroxyprogesterone Acetate and Dihydrotestosterone," Mol. Endocrinol., vol. 13, pp. 440-454 (1999); mend.endojournals.org.
Keown et al., "Methods for Introducing DNA into Mammalian Cells," Methods in Enzymology, 185:527-537 (1990).
Kingsman et al., "Replication in *Saccharomyces cerevisiae* of plasmid pBR313 carrying DNA from the yeast trpl region," Gene, 7: 141 (1979).
Kinoshita, H. et al. Methylation of the androgen receptor minimal promoter silences transcription in human prostate cancer. Cancer Res 60, 3623-30 (2000).
Klein, K.A. et al. Progression of metastatic human prostate cancer to androgen independence in immunodeficient SCID mice. Nat Med 3, 402-8 (1997).
Kousteni, S. et al. Nongenotropic, sex-nonspecific signaling through the estrogen or androgen receptors: dissociation from transcriptional activity. Cell 104, 719-30 (2001).
Krüger et al., "Synthese und Reaktionen von 1-(1-Cyanoalkyl)-1-hydroxyharnstoffen," Arch. Pharm. (Weinheim), vol. 311, pp. 39-47 (1978).
Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).
Li, P. et al. Heterogeneous expression and functions of androgen receptor co-factors in primary prostate cancer. Am J Pathol 161, 1467-74 (2002).
Linja, M.J. et al., "Amplification and overexpression of androgen receptor gene in hormone-refractory prostate cancer", Cancer Research, vol. 61 (May 1, 2001) pp. 3550-3555.
Lobaccaro, J.M. et al. Molecular modeling and in vitro investigations of the human androgen receptor DNA-binding domain: application for the study of two mutations. Mol Cell Endocrinol 116, 137-47 (1996).
Lu et al. "Molecular Mechanisms of Androgen-Independent Growth of Human Prostate Cancer LNCaP-Al Cells", Endocrinology 1999, vol. 140, No. 11, pp. 5054-5059.
Mammalian Cell Biotechnology: a Practical Approach, M. Butler, ed. (IRL Press, 1991).
Mancheva et al., "Preparation and Characterization of Diphenylindenonylthiohydantoin Derivatives of Non-Protein Cycloaliphatic Amino Acids," Dokladi na Bulgarskata Akademiya na Naukite (Comptes rendu de l'Academie bulgare des Sciences),vol. 45, No. 11, pp. 67-70 & title page (1992).
Manolagas et al., Sex steroids and bone. Recent Prog Horm Res 57, 385-409 (2002).
Mansour et al., "Disruption of the proto-oncogene int-2 in mouse embryo-derived stems cells: a general strategy for targeting mutations to non-selectable genes," Nature, 336:348-352 (1988).
Marhefka, et al., "Homology Modeling Using Multiple Molecular Dynamics Simulations and Docking Sudies of the Human Androgen Receptor Ligand Binding Domain Bound to Testosterone and Nonsteroidal Ligands," *J. Med. Chem.*, 44: 11, pp. 1729-1740 (2001).
Masiello et al., Bicalutamide functions as an androgen receptor antagonist by assembly of a transcriptionally inactive receptor. J Biol Chem 277, 26321-6 (2002).
Matias, et al., "Local Inhibition of Sebaceous Gland Growth by Topically Applied RU 58841," NY Acad. Sci., vol. 761, pp. 56-65 (1995).
Matias, P.M. et al. Structural basis for the glucocorticoid response in a mutant human androgen receptor (AR(ccr)) derived from an androgen-independent prostate cancer. J Med Chem 45, 1439-46 (2002).
Matias et al. Structural evidence for ligand specificity in the binding domain of the human androgen receptor. Implications for pathogenic gene mutations. J Biol Chem 275, 26164-71 (2000).

(56) References Cited

OTHER PUBLICATIONS

McDonnell et al. Expression of the protooncogene bcl-2 in the prostate and its association with emergence of androgen-independent prostate cancer. Cancer Res 52, 6940-4 (1992).

Migliaccio, A. et al. Steroid-induced androgen receptor-oestradiol receptor beta-Src complex triggers prostate cancer cell proliferation. Embo J 19, 5406-17 (2000).

Muller et al., "BCR first exon sequences specifically activate the BCR/ABL tyrosine kinase oncogene of Philadelphia chromosome-positive human leukemias," 1991, Mol. & Cell. Bio. 11:1785-1792.

Nakajima et al. Activated Dimethyl sulfoxide dehydration of amide and its application to one-pot preparation of benzyl-type prefluoroimidates. 2002. Tetrahedron. 58:3561-3577.

Nam et al., "Action of the Src Family Kinase Inhibitor, Dasatinib (BMS-354825), on Human Prostate Cancer Cells", Cancer Res., 2005, v. 65(20), pp. 9185-9189.

Navone, N. M., et al., "Model Systems of Prostate Cancer: Uses and Limitations" Cancer Metastasis, Kluwer Academic Publishers, Dordrecht, NL, 17 (4), 1999, pp. 361-371.

Nicole et al., "Synthèses D'Acides Aminés Cycliques À Partir de Dérivés de L'Acide Adipique," Canadian Journal of Chemistry, vol. 40, pp. 353-366 (1962).

NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251, printed Oct. 24, 2007.

Norris et al. Peptide antagonists of the human estrogen receptor. Science 285, 744-6 (1999).

Notice of Allowance from the U.S. Patent Office issued in U.S. Appl. No. 13/333,543 dated Mar. 19, 2013.

Notice of Allowance issued in U.S. Appl. No. 12/257,743 dated Mar. 28, 2013.

Notice of Allowance issued in U.S. Appl. No. 13/448,964 dated May 31, 2013.

Notice of Allowance issued in U.S. Appl. No. 11/730,168 mailed Sep. 20, 2011.

Notice of Allowance issued in U.S. Appl. No. 11/730,168 dated Jun. 10, 2011.

Notice of Allowance issued in U.S. Appl. No. 12/294,881 mailed Jun. 25, 2012.

Notice of Allowance issued in U.S. Appl. No. 12/708,531 mailed May 25, 2012.

Notice of Allowance with Examiner's Amendment in U.S. Appl. No. 10/583,280 mailed Jun. 9, 2011.

Notice of Allowance with Examiner's Amendment in U.S. Appl. No. 11/433,829 mailed Jun. 8, 2009.

Notice of Allowance with Examiner's Amendment in U.S. Appl. No. 11/433,829 mailed Nov. 18, 2009.

Notice of References Cited from U.S. Appl. No. 08/807,760 (1997).

Notice of References Cited of Jul. 24, 1992 from U.S. Patent and Trademark Office for U.S. Appl. No. 07/819,110.

Office Action (paper No. 10) from U.S. Patent and Trademark Office (USPTO) for U.S. Appl. No. 08/064,257 (mailed Sep. 27, 1994).

Office Action (paper No. 7) from U.S. Patent and Trademark Office (USPTO) for U.S. Appl. No. 08/064,257 (mailed Aug. 31, 1994).

Office Action from the U.S. Patent Office issued in U.S. Appl. No. 13/448,964 dated Feb. 28, 2013.

Office Action from the US Patent and Trademark Office (USPTO) issued in U.S. Appl. No. 13/333,543 mailed Jun. 12, 2012.

Office Action from the US Patent and Trademark Office (USPTO) issued in U.S. Appl. No. 13/448,964 dated Sep. 18, 2012.

Office Action in U.S. Appl. No. 10/583,280 mailed on Apr. 2, 2010.

Office Action in U.S. Appl. No. 10/583,280 mailed on Nov. 29, 2010.

Office Action in U.S. Appl. No. 12/257,743 mailed on Nov. 20, 2009.

Office Action issued in U.S. Appl. No. 12/708,531 dated Nov. 5, 2013.

Office Action issued in U.S. Appl. No. 13/619,280 dated Oct. 28, 2013.

Office Action issued in U.S. Appl. No. 10/590,445, mailed on Mar. 2, 2009.

Office Action issued in U.S. Appl. No. 11/433,829 mailed on Jan. 27, 2009.

Office Action issued in U.S. Appl. No. 12/708,531 mailed Nov. 14, 2011.

Office Action mailed Oct. 1, 2010 in U.S. Appl. No. 12/708,523.

Office Action mailed Oct. 8, 2010 in U.S. Appl. No. 11/730,168.

Office Action issued in U.S. Appl. No. 08/064,257 dated Jan. 18, 1994.

Office Action of Feb. 22, 1993 from U.S. Patent and Trademark Office for U.S. Appl. No. 07/819,110.

Office Action of Jun. 1, 1994 from U.S. Patent and Trademark Office for U.S. Appl. No. 07/819,110.

Office Action of Jun. 29, 2010 from U.S. Patent and Trademark Office for U.S. Appl. No. 12/257,743.

Office Action of Jul. 23, 2008 from U.S. Patent and Trademark Office for U.S. Appl. No. 10/590,445.

Office Action of Aug. 11, 2009 from U.S. Patent and Trademark Office for U.S. Appl. No. 10/583,280.

Office Action of Aug. 14, 1992 from U.S. Patent and Trademark Office for U.S. Appl. No. 07/819,110.

Office Action of Sep. 2, 1993 from U.S. Patent and Trademark Office for U.S. Appl. No. 07/819,110.

Oldfield et al., "The Chemistry and Pharmacology of a Ser4ies of Cycloalkanespiro-5'-hydantoins," Journal of Medical Chemistry, vol. 8, No. 2, pp. 239-249 (1965).

Ouk, S. et al., "Development of Androgen Receptor Inhibitors for Hormone-refractory Prostate Cancer", Prostate Cancer Foundation Meeting, Sep. 29-Oct. 1, 2005.

Park K. et al., "Metabolism of Fluorine-Containing Drugs," Annu. Rev. Pharmacol. Toxicol. 2001, vol. 41, pp. 443-470.

Patani et al., "Bioisosterism: A Rational Approach in Drug Design," Chem. Rev. 1996, vol. 96, pp. 3147-3176.

Paul et al., "Antiandrogen Withdrawal Syndrome Associated with Prostate Cancer Therapies: Incidence and Clinical Significance," Drug Safety, 2000 (5): 381-390.

Perou, C.M. et al. Molecular portraits of human breast tumors. Nature 406, 747-52 (2000).

Presentation of Charles Sawyers, Prostate Cancer Foundation Scientific Retreat, Scottsdale, Arizona, Sep. 29-Oct. 1, 2005.; C141.

Raffo et al. Overexpression of bcl-2 Protects Prostate Cancer Cells from Apoptosis in Vitro and Confers Resistance to Androgen Depletion in Vivo. Cancer Research. 1995. v. 55. 4438-4445.

Rao et al., "Merits and Considerations in the Use of Anti-Androgen," J. Steroid Biochem. 31 (4B), pp. 731-737 (1988).

Raynaud, "Action of a non-steroid anti-androgen, RU 23908, in peripheral and central tissues," J Steroid Biochem, 11 (1979) 93-99.

Remington: The Science and Practice of Pharmacy, 19th Edition, Gennaro (ed.) 1995, Mack Publishing Company, Easton, PA.

Restriction Requirement in U.S. Appl. No. 10/583,280 mailed on Aug. 11, 2009.

Restriction Requirement in U.S. Appl. No. 10/590,445 mailed on Jun. 5, 2008.

Restriction Requirement in U.S. Appl. No. 10/590,445 mailed on Mar. 26, 2008.

Restriction Requirement in U.S. Appl. No. 11/433,829 mailed on Nov. 3, 2008.

Restriction Requirement in U.S. Appl. No. 12/257,743 mailed on Jul. 6, 2009.

Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).

Sambrook et al., Molecular Cloning: A Laboratory Manual 2nd edition (1989) Cold Spring Harbor Laboratory Press, Cold Spring Harbor, N.Y.

Saunders,P.T., et al., "Point mutations detected in the androgen receptor gene of three men with partial androgen insensitivity syndrome", Clin. Endocrinol. (Oxf) 37 (3), 214-220 (1992).

(56) References Cited

OTHER PUBLICATIONS

Schaefer et al. Failure is an Option: Learning from Unsuccessful Proof-of-Concept Trials. 2008. Drug Discovery Today. 13:913-916.
Schellhammer, P.F. et al. Prostate specific antigen decreases after withdrawal of antiandrogen therapy with bicalutamide or flutamide in patients receiving combined androgen blockade. J Urol 157, 1731-5 (1997).
Scher et al. Antitumour activity of MDV3100 in castration-resistant prostate cancer: a phase 1-2 study. 2010. Lancet. 375:1437-1446.
Sderholm, et al., "Three-Dimensional Structure—Activity Relationships of Nonsteroidal Ligands in Complex with Androgen Receptor Ligand-Binding Domain," J. Med. Chem., vol. 48, No. 4, pp. 917-925 (2005).
Shang, Y. & Brown, M. Molecular determinants for the tissue specificity of SERMs. Science 295, 2465-8 (2002).
Shang, Y., Myers, M. & Brown, M. Formation of the androgen receptor transcription complex. Mol Cell 9, 601-10 (2002).
Shi, Xu-Bao, et al., "Functional analysis of 44 mutant androgen receptors from human prostate cancer", Cancer Research 62 (5), pp. 1496-1502 (Mar. 1, 2002).
Shiau, A.K. et al. The structural basis of estrogen receptor/coactivator recognition and the antagonism of this interaction by tamoxifen. Cell 95, 927-37 (1998).
Singh et al., "Androgen Receptor Antagonists (Antiandrogens): Structure-Activity Relationships", Current Medicinal Chemistry, 2000, 7, pp. 211-247.
Singh, "Amidine: Structure, Reactivity and Complexation Behaviour," Int'l J.of Chem. Tech. Res., vol. 1(2), pp. 250-264 (2009).
Sperry, et al., Androgen binding profiles of two distinct nuclear androgen receptors in Atlantic croaker (*Micropogonias undulates*), Journal of Steroid Biochemistry & Molecular Biology, vol. 73, pp. 93-103 (2000).
Stinchcomb et al., "Isolation and characterisation of a yeast chromosomal replicator," Nature, 282:39 (1979).
Su,Q.R., et al., "Polymorphisms of androgen receptor gene in childhood and adolescent males with first-onset major depressive disorder and associationwith related symptomatology", Int. J. Neurosci. 117 (7), 903-917 (2007).
Supplementary European Search in EP 07754060 mailed on Oct. 11, 2010.
Sweet,C.R., et al., "A unique point mutation in the androgen receptor gene in a family with complete androgen insensitivity syndrome", Fertil. Steril. 58 (4), 703-707 (1992).
Szelei et al. Androgen-Induced Inhibition of Proliferation in Human Breast Cancer MCF7 Cells Transfected with Androgen Receptor. Endocrinology. 1997. v. 138 (4). pp. 1406-1412.
Taplin, M.E. et al. Androgen receptor mutations in androgen-independent prostate cancer: Cancer and Leukemia Group B Study 9663. J Clin Oncol 21, 2673-8 (2003).
Taplin, M.E. et al. Mutation of the androgen-receptor gene in metastatic androgen-independent prostate cancer. N Engl J Med 332, 1393-8 (1995).
Taplin, M.E. et al. Selection for androgen receptor mutations in prostate cancers treated with androgen antagonist. Cancer Res 59, 2511-5 (1999).
Teutsch et al., "Non-steroidal Antiandrogens: Synthesis and Biological Profile of High-affinity Ligands for the Androgen Receptor," J. Steroid Biochem. Molec. Biol. 1994, 48, 111-119.
The Pharmacological Basis of Therapeutics, Goodman and Gilman, eds., Macmillan Publishing Co., New York (1980).
The Practice of Medicinal Chemistry, Wermuth et al., Ch 31, (Academic Press, 1996).
Tremblay et al., Ligand-independent recruitment of SRC-1 to estrogen receptor beta through phosphorylation of activation function AF-1. Mol Cell 3, 513-9 (1999).
Tschumper et al., "Sequence of a yeast DNA fragment containunng a chromosomal replicator and the TRP1 gene," Gene, 10: 157-166 (1980).
Umezawa et al., "The Synthesis of Cyclic α-Amino Acids," Bulletin of the Chemical Society of Japan, vol. 40, No. 1, pp. 209-214 & title page (1967).
Notice of Allowance issued in U.S. Appl. No. 13/333,543 dated Jun. 20, 2013.
Notice of Allowance, issued in U.S. Appl. No. 12/708,523, dated Dec. 16, 2011.
Notice of Allowance, issued in U.S. Appl. No. 12/708,523, dated Mar. 26, 2012.
Urlaub et al., "Isolation of Chinese hamster cell mutants deficient in dihydrofolate reductase activity," Proc. Natl. Acad. Sci. USA, 77:4216 (1980).
Van Dort et al., "Design, Synthesis, and Pharmacological Characterization of 4-[4,4-Dimethyl-3-(4-hydroxybutyl)-5-oxo-2-thioxo-1-imidazolidinyl]-2-iodobenzonitrile as a High-Affinity Nonsteroidal Androgen Receptor Ligand," J. Med. Chem. 2000, 43, 3344-3347.
Veldscholte, J. et al. A mutation in the ligand binding domain of the androgen receptor of human LNCaP cells affects steroid binding characteristics and response to anti-androgens. Biochem Biophys Res Commun 173, 534-40 (1990).
Visakorpi, T. et al. In vivo amplification of the androgen receptor gene and progression of human prostate cancer. Nat Genet 9, 401-6 (1995).
Wainstein, M.A. et al. CWR22: androgen-dependent xenograft model derived from a primary human prostatic carcinoma. Cancer Res 54, 6049-52 (1994).
Wallen et al., "Androgen Receptor Gene Mutations in Hormone-Refractory Prostate Cancer", J. Pathology 1999, vol. 189, pp. 559-563.
Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).
Wang, S. et al. Prostate-specific deletion of the murine Pten tumor suppressor gene leads to metastatic prostate cancer. Cancer Cell 4, 209-21 (2003).
Wooster,R., et al., "A germline mutation in the androgen receptor gene in two brothers with breast cancer and Reifenstein syndrome", Nat. Genet. 2 (2), 132-134 (1992).
Written Opinion issued in PCT Application No. PCT/US2007/007854, mailed on Apr. 15, 2008.
Written Opinion issued in PCT Application No. PCT/US2008/012149, mailed on Apr. 29, 2009.
Written Opinion issued in PCT Application No. PCT/US2004/042221, mailed on Jun. 20, 2005.
Written Opinion issued in PCT Application No. PCT/US2005/005529, mailed on Nov. 10, 2005.
Written Opinion issued in PCT Application No. PCT/US2006/011417, mailed on Jul. 3, 2006.
Written Opinion issued in PCT Application PCT/US2007/07485, mailed on Sep. 4, 2008.
Zajchowski et al. Estrogen inhibits the growth of estrogen receptor-negative, but not estrogen receptor-positive, human mammary epithelial cells expressing a recombinant estrogen receptor. 1993. Cancer Research. 53:5004-5011.
Zarghami, et al., "Steroid hormone regulation of prostate-specific antigen gene expression in breast cancer," British Journal of Cancer, vol. 75, No. 4, pp. 579-588 (1997).
Zhau, H.Y. et al. Androgen-repressed phenotype in human prostate cancer. Proc Natl Acad Sci U S A 93,15152-7 (1996).
Zhou et al., A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).
Zoppi,S., et al. "Amino acid substitutions in the DNA-binding domain of the human androgen receptor are a frequent cause of receptor-binding positive androgen resistance", Mol. Endocrinol. 6 (3), 409-415 (1992).
International Search Report and Written Opinion issued in International Application No. PCT/US2008/086171 dated Jul. 21, 2009.

(56) References Cited

OTHER PUBLICATIONS

Chen et al., "Antiandrogens and androgen depleting therapies in prostate cancer: novel agents for an established target," Lancet Oncol. 2009; 10 : 981-991.
Grossmann et al., "Androgen Receptor Signaling in Androgen-Refractory Prostate Cancer," J Natl Cancer Inst. 2001; 93 : 1687-1697.
Harris et al., "Androgen deprivation therapy: progress in understanding mechanisms of resistance and optimizing androgen depletion," Nat Clin Pract Urol. 2009; 6:76-85.
Higano et al., "New and emerging agents for the treatment of castration-resistance prostate cancer," Urol Oncol. 2011; 29 : S1-S8.
Hu et al., "Molecular processes leading to aberrant androgen receptor signaling and castration resistance in prostate cancer," Expert Rev. Endocrinol Metab. 2010; 5: 753-764.
Knudsen et al., "Starving the addiction: new opportunities for durable suppression of AR signaling in prostate cancer" Clin Cancer Res. 2009; 15: 4792-4798.
Scher et al., "Increased Survival with Enzalutamide in Prostate Cancer after Chemotherapy," N Engl J Med. 2012; 367: 1187-1197.
Schweizer et al., "Abiraterone and other novel androgen-directed strategies for the treatment of prostate cancer: a new era of hormonal therapies is born." Ther Adv Urol. 2012; 4: 167-178.
Tran et al., "Development of a Second-Generation Antiandrogen for Treatment of Advanced Prostate Cancer," Science. 2009; 324 : 787-790.
XTANDI [package insert]. Northbrook, IL: Astellas Pharma US, Inc; 2012.
Office Action issued in U.S. Appl. No. 14/138,001 dated Aug. 29, 2014.
Office Action issued in U.S. Appl. No. 13/619,280 dated May 28, 2014.
Office Action issued in U.S. Appl. No. 12/708,531 dated May 28, 2014.
Notice of Allowance issued in U.S. Appl. No. 13/448,964 dated Jul. 3, 2014.
Notice of Allowance issued in U.S. Appl. No. 10/590,445 dated Dec. 22, 2009.
Notice of Allowance issued in U.S. Appl. No. 13/333,543 dated Oct. 23, 2012.
Notice of Allowance issued in U.S. Appl. No. 13/333,543 dated Sep. 23, 2013.
Notice of Allowance issued in U.S. Appl. No. 12/257,743 dated Nov. 19, 2013.
Notice of Allowance issued in U.S. Appl. No. 12/257,743 dated Jul. 1, 2013.
Restriction Requirement issued in U.S. Appl. No. 13/619,280 dated Aug. 9, 2013.
Notice of Allowance issued in U.S. Appl. No. 13/448,964 dated Sep. 20, 2013.
Notice of Allowance issued in U.S. Appl. No. 13/448,964 dated Oct. 22, 2014.
Notice of Allowance issued in U.S. Appl. No. 12/708,531 dated Jan. 9, 2015.
Notice of Allowance issued in U.S. Appl. No. 12/708,531 dated Jul. 12, 2013.
Notice of Allowance issued in U.S. Appl. No. 13/619,280 dated Jan. 9, 2015.
Notice of Allowance issued in U.S. Appl. No. 13/448,964 dated Mar. 27, 2015.
Notice of Allowance issued in U.S. Appl. No. 14/138,001 dated Mar. 11, 2015.
Office Action issued in U.S. Appl. No. 14/496,973 dated Feb. 11, 2015.
European Search Report issued in European Application No. 11178889.9 dated Nov. 17, 2011.
European Search Report issued in European Application No. 11181133.7 dated Mar. 14, 2012.
European Search Report issued in European Application No. 11184401.5 dated Mar. 28, 2012.
European Search Report issued in European Application No. 78101244.8 (1979).
European Search Report issued in European Application No. 90403725.6 (1991).
Third Party Observation Patent Eye Report filed in European patent application 20060748863 by "Patent Eye" on Jun. 5, 2014.
"Patent Risk at Medivation, Inc.", "Patent Eye", http://web.archive.org/web/*/http://www.scribd.com/doc/153462932/Patent-Risk-at-Medivation-Inc, saved Jul. 18, 2013, retrieved Apr. 16, 2014 (no longer available on website as of Jan. 29, 2015).
Statement of Grounds and Particulars re Opposition to Australian patent application 2006248109 dated Apr. 11, 2013.
Notice of Opposition re Australian patent application 2006248109 dated Jan. 11, 2013.
Patent office letter re Notice of Opposition re Australian patent application 2006248109 dated Jan. 15, 2013.
Application for Extension of Time re Opposition to Australian patent application 2006248109 dated Jul. 10, 2013.
Letter from D. Beadle to Australian patent office withdrawing Opposition to Australian patent application 2006248109 dated Oct. 11, 2013.
Patent office letter indicating withdrawal of Opposition to Australian patent application 2006248109 dated Oct. 15, 2013.
Australian Official Journal of Patents (Supplement) publication of Oct. 24, 2013 indicating withdrawal of Opposition to Australian patent application 2006248109.
EPO Summons to Attend Oral Proceedings re Opposition to European patent 1893196 dated Jun. 20, 2014.
Brief EPO Communication re Opposition to European patent 1893196 dated Nov. 10, 2014.
Brief EPO Communication re Opposition to European patent 1893196 dated Nov. 5, 2014.
EPO Interlocutory Decision re Opposition to European patent 1893196 dated Nov. 25, 2014.
Notice of Opposition re European patent 1893196 dated Oct. 18, 2012.
Opposition to European patent 1893196 dated Oct. 18, 2012.
European patent 1893196 as upheld in Interlocutory Decision dated Nov. 25, 2014.
Letter re withdrawal of request for oral proceedings re Opposition to European patent 1893196 dated Oct. 30, 2014.
Letter from Proprietor re Opposition to European patent 1893196 dated Oct. 29, 2014.
Brief EPO Communication re Opposition to European patent 1893196 dated Sep. 30, 2013.
Request for extension of time re Opposition to European patent 1893196 dated Sep. 24, 2013.
EPO Communication re extension of time re Opposition to European patent 1893196 dated Sep. 30, 2013.
Brief EPO Communication re Opposition to European patent 1893196 dated Sep. 26, 2014.
Letter re Opposition to European patent 1893196 dated Sep. 30, 2014.
Brief EPO Communication re Opposition to European patent 1893196 dated Oct. 30, 2014.
Letter from Proprietor re Opposition to European patent 1893196 dated Oct. 2, 2014.
EPO Communication re Opposition to European patent 1893196 dated May 31, 2013.
Response to Opposition re European patent 1893196 dated May 24, 2013.
Response to Opposition re European patent 1893196 dated May 24, 2013: Main Request clean.
Response to Opposition re European patent 1893196 dated May 24, 2013: Main Request marked.
Response to Opposition re European patent 1893196 dated May 24, 2013: 1st Auxiliary Request clean.
Response to Opposition re European patent 1893196 dated May 24, 2013: 1st Auxiliary Request marked.
Response to Opposition re European patent 1893196 dated May 24, 2013: 2nd Auxiliary Request clean.
Response to Opposition re European patent 1893196 dated May 24, 2013: 2nd Auxiliary Request marked.

(56) References Cited

OTHER PUBLICATIONS

Response to Opposition re European patent 1893196 dated May 24, 2013: FDA approval letter of Aug. 31, 2012.
Response to Opposition re European patent 1893196 dated May 24, 2013: EMEA approval letter of Apr. 25, 2013.
Response to Opposition re European patent 1893196 dated May 24, 2013: Medivation press release of Apr. 26, 2013.
Response to Opposition re European patent 1893196 dated May 24, 2013: Medivation press release of Aug. 31, 2012.
Response to Opposition re European patent 1893196 dated May 24, 2013: FDA press release of Aug. 31, 2012.
Response to Opposition re European patent 1893196 dated May 24, 2013: Medivation press release of May 9, 2013.
First Examination Report re Indian patent application 9668/DELNP/2007 dated May 24, 2013.
Response to First Examination Report re Indian patent application 9668/DELNP/2007 dated Feb. 7, 2014.
Third Party (Ecolec) letter re Indian patent application 9668/DELNP/2007 dated Aug. 28, 2012.
Fresenius Pre-Grant Opposition re Indian patent application 9668/DELNP/2007 dated Dec. 1, 2012.
Fresenius Pre-Grant Opposition re Indian patent application 9668/DELNP/2007 dated Dec. 1, 2012: Annexure I, Claims.
Fresenius Pre-Grant Opposition re Indian patent application 9668/DELNP/2007 dated Dec. 1, 2012: Annexure II, Statement under Section 8 re IN 9668/DELNP/2007 of Dec. 13, 2007.
Fresenius Pre-Grant Opposition re Indian patent application 9668/DELNP/2007 dated Dec. 1, 2012: Annexure III, Espacenet family list WO2006124118(A1).
Fresenius Pre-Grant Opposition re Indian patent application 9668/DELNP/2007 dated Dec. 1, 2012: Annexure IV, European Patent Office Communication re EP 06 748 863.5-1211 of Nov. 11, 2010.
Letter from Indian patent office dated May 24, 2013 reporting Fresenius Pre-Grant Opposition re Indian patent application 9668/DELNP/2007.
Response to Fresenius Pre-Grant Opposition re Indian patent application 9668/DELNP/2007 dated Aug. 23, 2013.
Response to Fresenius Pre-Grant Opposition re Indian patent application 9668/DELNP/2007 dated Aug. 23, 2013: Annexure G, Medivation press release of Jun. 24, 2013.
Response to Fresenius Pre-Grant Opposition re Indian patent application 9668/DELNP/2007 dated Aug. 23, 2013: Annexure H, European Commission adoption of decision granting marketing authorization of Jun. 21, 2013.
Response to Fresenius Pre-Grant Opposition re Indian patent application 9668/DELNP/2007 dated Aug. 23, 2013: Annexure L, Submission of Form 3 on Apr. 27, 2009 and submission of Form 3 on Jun. 24, 2008 to Indian patent office for IN 9668/DELNP/2007.
Response to Fresenius Pre-Grant Opposition re Indian patent application 9668/DELNP/2007 dated Aug. 23, 2013: Annexure M, Letter of Aug. 16, 2013 to Indian patent office for IN 9668/DELNP/2007.
Response to Fresenius Pre-Grant Opposition re Indian patent application 9668/DELNP/2007: Affidavit and Curriculum Vitae of Josh Schafer dated Aug. 19, 2014.
BDR Pre-Grant Opposition documents re Indian patent application 9668/DELNP/2007 dated Jul. 22, 2013.
BDR Pre-Grant Opposition documents re Indian patent application 9668/DELNP/2007 dated Jul. 22, 2013: Annexure IX, Bibliographic data for AT541571, AU2006248109A1, AU2007245022A1, PI0610359-6A2, PI0709682-8A2, CA2608436, CA2648139, CN101222922(A), CN101460467(A), CN102584712(A), CN102755318(A), DK1893196(T3), EP1893196A0, EP2013187A0, EP2439196A1, EP2444085A1, EP2561871A1, ES2378778, HK1112856(A1), HRP20120323T1, JP2008540523(A), JP2011068653(A), JP2012236843(A), JP2009531449(A), and JP2012211190(A).
BDR Pre-Grant Opposition documents re Indian patent application 9668/DELNP/2007 dated Jul. 22, 2013: Annexure X, Statement under Section 8 dated Dec. 13, 2007.

Response to BDR Pre-Grant Opposition re Indian patent application 9668/DELNP/2007 dated Jan. 23, 2014, including Annexures A-D.
Letter and Form 3 of Jan. 23, 2014 provided to Indian pat. office re IN pat. app. 9668/DELNP/2007.
Letter of Jan. 10, 2014 provided to Indian pat. office re IN pat. app. 9668/DELNP/2007.
Letter of Jan. 23, 2014 provided to Indian pat. office re IN pat. app. 9668/DELNP/2007.
Response to BDR Pre-Grant Opposition re Indian patent application 9668/DELNP/2007 dated Jan. 23, 2014: Declaration and Curriculum Vitae of Prof. M.E. Jung.
Response to BDR Pre-Grant Opposition re Indian patent application 9668/DELNP/2007 dated Jan. 23, 2014: Declaration and Curriculum Vitae of Dr. C.L. Sawyers.
Supplementary Appendix to Scher et al., "Increased survival with enzalutamide in prostate cancer after chemotherapy", N. Engl. J. Med., 367 (2012) 1187-97.
Supporting Online Material for Tran et al., "Development of a Second-Generation Antiandrogen for Treatment of Advanced Prostate Cancer", Science, 324 (2009) 787-790.
Pre-Grant BDR Opposition re Indian patent application 9668/DELNP/2007, Opponent Rejoinder dated Apr. 25, 2014.
Pre-Grant BDR Opposition re Indian patent application 9668/DELNP/2007, Opponent Rejoinder dated Apr. 25, 2014: Exhibit I and I(a), Affidavit and Resume of G.R. Wader.
Response to BDR Pre-Grant Opposition re Indian patent application 9668/DELNP/2007: Affidavit and Curriculum Vitae of Josh Schafer dated Aug. 28, 2014.
Astellas Annual Report 2013.
DiMasi et al., "The price of innovation: new estimates of drug development costs", J. Health Economics, 22 (2003) 151-185.
Pharmaceutical Research and Manufacturers of America, "2013 profile Biopharmaceutical Research Industry", Jul. 2013.
BDR Pre-Grant Opposition re Indian patent application 9073/DELNP/2008 dated Sep. 6, 2013.
BDR Pre-Grant Opposition re Indian patent application 9073/DELNP/2008 dated Sep. 6, 2013: Annexures I-II, Publication of Indian Patent Application 9073/DELNP/2008 A dated Mar. 20, 2009.
BDR Pre-Grant Opposition re Indian patent application 9073/DELNP/2008 dated Sep. 6, 2013: Annexure V, Publication of Indian Patent Application 9668/DELNP/2007 A dated Jun. 20, 2008.
BDR Pre-Grant Opposition re Indian patent application 9073/DELNP/2008 dated Sep. 6, 2013: Annexure VII, Bibliographic data for AU2007245022A1, BRPI0709682, CA2648139, CN101460467(A), CN102755318(A), EP2013187(A2), and JP2009531449(A).
BDR Pre-Grant Opposition re Indian patent application 9073/DELNP/2008 dated Sep. 6, 2013: Annexure VIII, Statement under Section 8 dated Oct. 24, 2008.
Shah Pre-Grant Opposition re Indian patent application 9668/DELNP/2007: Letter of Feb. 3, 2015.
Shah Pre-Grant Opposition re Indian patent application 9668/DELNP/2007 dated Feb. 3, 2015.
Shah Pre-Grant Opposition re Indian patent application 9668/DELNP/2007 dated Feb. 3, 2015: Annexure III, Amended claims of Indian patent applic. No. 9668/DEL/2007 of Feb. 11, 2014.
Shah Pre-Grant Opposition re Indian patent application 9668/DELNP/2007 dated Feb. 3, 2015: Annexure V, Indian patent applic. No. 2440/DEL/1996 filed Jun. 11, 1996.
Shah Pre-Grant Opposition re Indian patent application 9668/DELNP/2007 dated Feb. 3, 2015: Annexure XI, Decision of Ld. Controller in the Matter of Indian Patent Application No. 6087/DELNP/2005 dated Jan. 13, 2015.
"Statement of Facts & Arguments," Opposition Statement against European Patent No. 2444085B1, dated Dec. 18, 2015.
A Textbook of Drug Design and Development, ed. P. Krogsgaard-Larsen et al., 1992, Harwood Academic Publishers, pp. 610-611.
Applicant Initiated Interview Summary issued in U.S. Appl. No. 13/448,964 dated Feb. 1, 2013.
Applicant Written Submission re BDR Pre-Grant Opposition re Indian patent application 9668/DELNP/2007 dated Sep. 14, 2015 with Appendices.

(56) References Cited

OTHER PUBLICATIONS

Applicant Written Submission re Fresenius Pre-Grant Opposition re Indian patent application 9668/DELNP/2007 dated Sep. 11, 2015 with Appendices.
Applicant Written Submission re Umesh Shah Pre-Grant Opposition re Indian patent application 9668/DELNP/2007 dated Sep. 11, 2015 with Appendices.
Assignment filed in U.S. Appl. No. 11/433,829, recorded on Jun. 22, 2009 as Reel/Frame No. 023463/0018.
Bohl et al., "A Ligand-Based Approach to Identify Quantitative Structure-Activity Relationships for the Androgen Receptor," J. Med. Chem. 2004, 47, 3765-3776.
First Examination Report re Indian patent application 9073/DELNP/2008 dated Mar. 30, 2015.
Handouts by Opponent Fresenius Kabi to Indian Patent Office during Oral Hearings before the Indian Patent Office dated Jul. 2-3, 2015, re Fresenius Kabi Opposition re Indian patent application 9668/DELNP/2007.
Information Disclosure Statement filed in U.S. Appl. No. 11/433,829, dated Oct. 9, 2009.
Notice of Allowance issued in U.S. Appl. No. 13/448,964, dated Mar. 26, 2014.
Notice of Allowance issued in U.S. Appl. No. 13/619,280, dated Oct. 13, 2015.
Notice of Allowance issued in U.S. Appl. No. 14/138,001, dated Jun. 12, 2015.
Notice of Allowance issued in U.S. Appl. No. 14/138,001, dated Sep. 22, 2015.
Notice of Allowance issued in U.S. Appl. No. 14/496,973, dated Nov. 19, 2015.
Notice of Allowance issued in U.S. Appl. No. 12/708,531, dated Oct. 27, 2015.
Notice of Allowance issued in U.S. Appl. No. 11/730,168, dated Dec. 22, 2011.
Notice of Allowance issued in U.S. Appl. No. 11/730,168, dated Jan. 19, 2012.
Notice of opposition to a European Patent, against European Patent No. 2444085B1, dated Dec. 18, 2015.
Pawar Pre-Grant Opposition re Indian patent application 9668/DELNP/2007 dated Jul. 27, 2015.
PCT Request form for PCT/US2006/011417 dated Mar. 29, 2006.
Record of U.S. Appl. No. 11/433,829, recorded on Jun. 24, 2009 as Reel/Frame No. 022867/0681.
Record of U.S. Appl. No. 11/433,829, recorded on Jun. 24, 2009 as Reel/Frame No. 022867/0741.
Record of U.S. Appl. No. 11/433,829, recorded on Nov. 16, 2009 as Reel/Frame No. 023523/0895.
Response to Shah Pre-Grant Opposition re Indian patent application 9668/DELNP/2007 dated May 19, 2015, including Annexures A-H.
Response to Shah Pre-Grant Opposition re Indian patent application 9668/DELNP/2007 dated May 19, 2015: Declaration and Curriculum Vitae of Dr. C.L. Sawyers.
Response to Shah Pre-Grant Opposition re Indian patent application 9668/DELNP/2007 dated May 19, 2015: Declaration and Curriculum Vitae of Prof. M.E. Jung.
Response to Shah Pre-Grant Opposition re Indian patent application 9668/DELNP/2007 dated May 19, 2015: FDA Approval Package for Xtandi®, Aug. 31, 2012 (10 pages).
Response to Shah Pre-Grant Opposition re Indian patent application 9668/DELNP/2007 dated May 19, 2015: Scher et al., "Increased Survival with Enzalutamide in Prostate Cancer after Chemotherapy", N. Engl. J. Med., 367(13) (2012) 1187-1197 with Supplemental Appendix (17 pages).
Response to Shah Pre-Grant Opposition re Indian patent application 9668/DELNP/2007 dated May 19, 2015: Scher n. et al., "Antitumour activity of MDV3100 in castration-resistant prostate cancer: a phase 1-2 study", Lancet, 375(9724) (2010) 1437-1446 (printed as 19 pages).
Response to Shah Pre-Grant Opposition re Indian patent application 9668/DELNP/2007 dated May 19, 2015: Tran et al., Development of a Second-Generation Antiandrogen for Treatment of Advanced Prostate Cancer, Science, 324(#5928) (May 8, 2009) 787-790 (printed as 11 pages) with Supporting Online Material (19 pages).
Slides submitted by Applicant to Indian Patent Office during Oral Hearings before the Indian Patent Office on Jul. 2-3, 2015 re Fresenius Kabi, BDR, and Umesh Shah Oppositions re Indian patent application 9668/DELNP/2007 (3 pages).
Slides presented by Applicant to Indian Patent Office during Oral Hearings before the Indian Patent Office on Jul. 2-3, 2015 re Fresenius Kabi, Bdr, and Umesh Shah Oppositions re Indian patent application 9668/Delnp/2007 (45 pp.).
Notice of Allowance issued in U.S. Appl. No. 14/138,001 dated Apr. 11, 2016.
Notice of Allowance issued in U.S. Appl. No. 14/496,973 dated Aug. 3, 2015.
Communication of Notices of Opposition to European Patent Applic. 11184401.5 (EP Patent 2444085), European Patent Office, Jan. 27, 2016.
Response to Pawar Pre-Grant Opposition re Indian patent application 9668/DELNP/2007 dated Mar. 15, 2016.
Response to First Examination Report re Indian patent application 9073/DELNP/2008 dated Mar. 22-23, 2016, including Form 1, Form 3 with Annexure, two Requests for Correction of Irregularity under Rule 137, copy of amended claims, copy of claims of 9668/DELNP/2007.
Letters to Indian Patent Office re Indian patent application 9073/DELNP/2008 of Mar. 2, 2016 and Mar. 8, 2016 with Annexure.
Notice of Allowance issued in U.S. Appl. No. 14/138,001, dated Jan. 21, 2016.
Notice of Withdrawal from Issue in U.S. Appl. No. 14/138,001, dated Feb. 24, 2016.
Indian Pharmaceutical Alliance Pre-Grant Opposition re Indian patent application 9668/DELNP/2007 dated Jan. 7, 2016.
Notice of Allowance issued in U.S. Appl. No. 14/496,973 dated Jun. 15, 2016.
Response to Indian Pharmaceutical Alliance Pre-Grant Opposition re Indian patent application No. 9668/DELNP/2007 dated Jul. 6, 2016.
Slides presented by Applicant to Indian Patent Office during Oral Hearings before the Indian Patent Office on Jul. 25, 2016 re Indian Pharmaceutical Alliance Pre-Grant Opposition re Indian patent application No. 9668/DELNP/2007 (45 pages).
*Merck v. Glenmark Pharm.*, (Oct. 7, 2015) High Ct. Delhi, CS (OS) 586/2013 (India).
*Parikumar v. Controller General of Patents*, (Jan. 23, 2013) Intell. Prop. App. Bd., OA/60/2012/PT/DEL (India).
*Roche v. Cipla*, (Dec. 8, 2015) High Ct. Delhi, RFA(OS) 92/2012 (India).
Applicant Written Submission re Indian Pharmaceutical Alliance Pre-Grant Opposition re Indian patent application No. 9668/DELNP/2007 dated Aug. 1, 2016.
Applicant Written Submission re Sheela Pawar Pre-Grant Opposition re Indian patent application No. 9668/DELNP/2007 dated Aug. 1, 2016.
EPO Final Decision re Opposition to European patent 1893196 dated Mar. 7, 2015.
EPO Communication 82(2) Final Decision re Opposition to European patent 1893196 dated Mar. 19, 2015 with Annex.
Battmann et al., "RU 58841, A New Specific Topical Antiandrogen: A Candidate of Choice for the Treatment of Acne, Androgenetic Alopecia and Hirsutism", J. Steroid Biochem Molec. Biol, 48(1) (1994) 55-60.
Thavonekham, "A Practical Synthesis of Ureas from Phenyl Carbamates", Synthesis, (Oct. 1997) 1189-1194.
Fresenius Written Submission re Opposition re Indian patent application 9668/DELNP/2007 dated Jul. 24, 2015 with Appendices.
BDR Written Submission re Opposition re Indian patent application 9668/DELNP/2007 dated Apr. 18, 2016 (letter dated Apr. 14, 2016) with Appendices.
Documents presented by BDR before Indian Patent Office on Jul. 2-3, 2015, re BDR Opposition re Indian patent application 9668/DELNP/2007.

(56) References Cited

OTHER PUBLICATIONS

Document presented by Fresenius Kabi before Indian Patent Office on Jul. 2-3, 2015, re Fresenius Kabi Opposition re Indian patent application 9668/DELNP/2007.
Pawar Written Submission re Opposition re Indian patent application 9668/DELNP/2007 dated Aug. 1, 2016 with Appendices.
Response to Fresenius Pre-Grant Opposition re Indian patent application 9668/DELNP/2007: Submissions to Indian patent office of Apr. 3, 2014—Affidavit (signed Feb. 11, 2014) & Curriculum Vitae of Charles L. Sawyers and Affidavit (signed Jan. 22, 2014) & Curriculum Vitae of Michael E. Jung.
Notice of Allowance issued in U.S. Appl. No. 14/138,001, dated Aug. 26, 2016.
Notice of Allowance issued in U.S. Appl. No. 13/619,280, dated Aug. 26, 2016.
Wong, C.-I. et al., "Androgen Receptor Antagonist versus Agonist Activities of the Fungicide Vinclozolin Relative to Hydroxyflutamide", J. Biol. Chem., 270(34) (1995) 19998-20003.
Notice of Allowance in U.S. Appl. No. 12/708,531, dated Oct. 26, 2016.
Notice of Allowance in U.S. Appl. No. 13/619,280, dated Nov. 7, 2016.
Notice of Allowance in U.S. Appl. No. 14/496,973, dated Sep. 27, 2016.
Indian Patent Office Order re Application 9668/DELNP/2007, dated Nov. 8, 2016.
Yin et al., "Key Structural Features of Nonsteroidal Ligands for Binding and Activation of the Androgen Receptor", Mol. Pharmacol. 63(1) (2003) 211-223.
Van Dort et al., "Synthesis and Structure-Activity Studies of Side-Chain Derivatized Arylhydantoins for Investigation as Androgen Receptor Radioligands", Bioorganic & Medicinal Chemistry Letters 11 (2001) 1045-1047.
Silverman, The Organic Chemistry of Drug Design and Drug Action, Academic Press, Inc. (1992) pp. 19-23.
Gao et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia", Endocrinology, 145(12) (Dec. 2004) 5420-5428 (pub. online Aug. 12, 2004).
Lipinski et al., "Experimental and Computational Approaches to Estimate Solubility and Permeability in Drug Discovery and Development Settings," Advanced Drug Delivery Reviews, 46 (2001) pp. 3-26.
Lipinski et al., "Experimental and Computational Approaches to Estimate Solubility and Permeability in Drug Discovery and Development Settings," Advanced Drug Delivery Reviews, 23 (1997) pp. 3-25.
Rowe et al. (Ed.)., Handbook of Pharmaceutical Excipients, 4th Edition (2003) pp. 219-221, 454- 459, and 672-676.
Rau et al., "The mechanisms and managements of hormone-therapy resistance in breast and prostate cancers," Endocr Relat Cancer, 12 (Sep. 1, 2005) 511-532.
Kinoyama et al., "N-Arylpiperazine-I-carboxamide Derivatives: a Novel Series of Orally Active Nonsteroidal Androgen Receptor Antagonists", Chem. Pharm. Bull., 53(4) (2005) 402-409.
Listing of Chemical Abstracts search presented by Examiner Michael P. Barker with Oct. 8, 2010 Office Action for U.S. Appl. No. 11/730,168.
Kingsman, A.J. et al., "Replication in *Saccharomyces cerevisiae* of Plasmid pBR313 Carrying DNA from the Yeast trpl Region", Gene 7 (1979) 141-152.
XTANDI [package insert]. Northbrook, IL: Astellas Pharma U.S., Inc.; 2014.
Information Disclosure Statement filed in U.S. Appl. No. 11/433,829 on Oct. 9, 2009.
Written Opinion issued in International Applic. No. PCT/US2004/042258 dated Aug. 7, 2006.

Applicant Writ Petition (Civil, No. 1163 of 2017) re Indian Patent Application No. 9668/DELNP/2007 filed in Delhi High Court, India, dated Jan. 31, 2017.
Union of India (Respondent No. 1) and Assistant Controller of Patents & Designs (Respondent No. 2) Counter Affidavit for Writ Petition (Civil, No. 1163 of 2017) filed in Delhi High Court, India, dated May 1, 2017.
Fresenius Kabi Oncology Limited (Respondent No. 3) Counter Affidavit for Writ Petition (Civil, No. 1163 of 2017) filed in Delhi High Court, India, dated Aug. 1, 2017.
BDR Pharmaceutical International Pvt. Ltd. (Respondent No. 4) Counter Affidavit for Writ Petition (Civil, No. 1163 of 2017) filed in Delhi High Court, India, dated Apr. 25, 2017.
Umesh Shah (Respondent No. 5) Counter Affidavit for Writ Petition (Civil, No. 1163 of 2017) filed in Delhi High Court, India, dated Apr. 29, 2017.
Indian Pharmaceutical Alliance (Respondent No. 7) Counter Affidavit for Writ Petition (Civil, No. 1163 of 2017) filed in Delhi High Court, India, dated Jul. 19, 2017.
Applicant Rejoinder to Counter Affidavit of Union of India (Respondent No. 1) and Assistant Controller of Patents & Designs (Respondent No. 2) for Writ Petition (Civil, No. 1163 of 2017) filed in Delhi High Court, India, dated Jun. 27, 2017.
Applicant Rejoinder to Counter Affidavit of BDR Pharmaceutical International Pvt. Ltd. (Respondent No. 4) for Writ Petition (Civil, No. 1163 of 2017) filed in Delhi High Court, India, dated Jun. 27, 2017.
Applicant Rejoinder to Counter Affidavit of Umesh Shah (Respondent No. 5) for Writ Petition (Civil, No. 1163 of 2017) filed in Delhi High Court, India, dated Jun. 27, 2017.
U.S. Appl. No. 15/655,458, filed Jul. 20, 2017.
Notice of Allowance in U.S. Appl. No. 13/619,280, dated Jun. 6, 2017.
Notice of Allowance in U.S. Appl. No. 14/138,001, dated Mar. 6, 2017.
Notice of Allowance in U.S. Appl. No. 14/496,973, dated Apr. 20, 2017.
Lehmann et al., "Identification of human triple-negative breast cancer subtypes and preclinical models for selection of targeted therapies", J.Clin. Invest. 121(7) (2011) 2750-2776 (8 pages).
De Amicis et al., "Androgen Receptor Overexpression Induces Tamoxifen Resistance in Human Breast Cancer Cells", Breast Cancer Res. Treat., 121(1) (2010) 1-11.
"Tamoxifen", Wikipedia, https:/en.wikipedia.org/wiki/tamoxifen, accessed Aug. 18, 2017 (13 pages).
Zhang et al., "Metabolite Identification and Profiling in Drug Design: Current Practice and Future Directions", Current Pharmaceutical Design, 15 (2009) 2220-2235.
Cheng et al., "Lead Optimization in Discovery Drug Metabolism and Pharmacokinetics/Case study: The Hepatitis C Virus (HCV) Protease Inhibitor SCH 503034", Perspectives in Medicinal Chemistry, 1 (2007) 1-9.
Testa, "Chapter 6: Monooxygenase-Catalyzed N-C Cleavage" in "The Metabolism of Drugs and Other Xenobiotics: Biochemistry of Redox Reactions", Academic Press (1995) Eds. Testa & Caldwell, Cover and Bibliographic pages and pp. 203-234.
Tang et al., "Drug Metabolism and Pharmacokinetics in Support of Drug Design", Current Pharmaceutical Design, 15 (2009) 2170-2183.
"Animal Models in Toxicology", CRC Press (2007) 2nd ed., Ed. Shayne C. Gad, Cover and Bibliographic pages and pp. 122-130.
Mihic et al., "Chapter 17:Hypnotics and Sedatives" in "Goodman & Gilman's: The Pharmacological Basis of Therapeutics", 12th ed.
Perrin et al., "Metabolism of N-methyl-amide by cytochrome P450s: Formation and characterization of highly stable carbinolamide intermediate", FEBS Journal, 278 (2011) 2167-2178.
Fura et al., "Discovering Drugs through Biological Transformation: Role of Pharmacologically Active Metabolites in Drug Discovery", J. Med, Chem., 2011, 47(18) (2004) 4339-4351.
Fura, "Role of pharmacologically active metabolites in drug discovery and development", Drug Discovery Today, 11(3-4) (2006) 133-142.

(56) References Cited

OTHER PUBLICATIONS

Bennett et al., "Validation of a method for quantifying enzalutamide and its major metabolites in human plasma by LC-MS/MS", Bioanalysis, 6(6) (2014) 737-744.
Yevich, A Textbook of Drug Design and Development, Ed., Krogsgaard-Larsen et al., Harwood Academic Publishers (1992) Cover & Bibliographic pages & pp. 610-611 & 614-615.
Miller, "Structure-Activity Relationship and Drug Design" in "Remington: The Science and Practice of Pharmacy", 20th ed., Lippincott (2000) pp. 458-461.
Mandela et al., "The norepinephrine transporter and its regulation", J. Neurochemistry, 97(2) (2006) 310-333.
Kedderis et al., "Peroxidase-catalyzed N-demethylation reactions: deuterium solvent isotope effects", Biochemistry, 24 (1985) 6158-6163.
Miwa et al., "The use of intramolecular isotope effects to distinguish between deprotonation and hydrogen atom abstraction mechanisms in cytochrome P-450 and peroxidase-catalyzed N-demethylation reactions", J. Biol. Chem., 258(23) (1983) 14445-14449.
Chen et al., "Oxidative N-dealkylation of p-cyclopropyl-N,N-dimethylaniline. A substituent effect on a radical-clock reaction rationalized by ab initio calculations on radical cation intermediates", J. Org. Chem., 62(23) (1997) 8227-8230.
EMA CHMP assessment report (EMA/CHMP/383457/2013) "Xtandi: enzalutamide", Apr. 25, 2013.
Leighton et al., Center for Drug Evaluation and Research, App. No. 203415 Orig 1s000, Pharmacology Reviews, Memorandum on Xtandi® (Enzalutamide), Aug. 22, 2012.
Guidance for Industry: Safety Testing of Drug Metabolites, FDA, Feb. 2008.
Guidance for Industry: General Considerations for the Clinical Evaluation of Drugs, FDA, Feb. 1997.
Hans-Joachim Böhm et al., "Fluorine in Medicinal Chemistry," ChemBioChem, 5(5) (May 3, 2004) 637-643.
Actavis Notification of Certification for U.S. Pat. Nos. 7,709,517, 8,183,274, and 9,126,941 Pursuant to 21 U.S.C. 355(j)(2)(a)(vii)(IV) ("Paragraph IV Certification"): Letter and Detailed Factual and Legal Bases of Oct. 24, 2016.
Apotex Notification of Certification for U.S. Pat. Nos. 7,709,517, 8,183,274, and 9,126,941 Pursuant to 21 U.S.C. 355(j)(2)(a)(vii)(IV) ("Paragraph IV Certification"): Letter and Detailed Factual and Legal Bases of Nov. 1, 2016.
Zydus Notification of Certification for U.S. Pat. Nos. 7,709,517, 8,183,274, and 9,126,941 Pursuant to 21 U.S.C. 355(j)(2)(a)(vii)(IV) ("Paragraph IV Certification"): Letter and Detailed Factual and Legal Bases of Nov. 1, 2016.
Roxane Laboratories Notification of Certification for U.S. Pat. Nos. 7,709,517, 8,183,274, and 9,126,941 Pursuant to 21 U.S.C. 355(j)(2)(a)(vii)(IV) ("Paragraph IV Certification"): Letter and Factual and Legal Basis of Apr. 12, 2017.
Notice of Allowance in U.S. Appl. No. 14/138,001, dated Oct. 6, 2017.
Applicant Rejoinder to Counter Affidavit of Fresenius Kabi Oncology Limited (Respondent No. 3) for Writ Petition (Civil, No. 1163 of 2017) filed in Delhi High Court, India, dated Dec. 2, 2017.
Applicant Rejoinder to Counter Affidavit of Indian Pharmaceutical Alliance (Respondent No. 7) for Writ Petition (Civil, No. 1163 of 2017) filed in Delhi High Court, India, dated Dec. 2, 2017.
Chande, M. S. et al., "Synthesis of new imidazolidinones, spiro-imidazolidinones and spiro-hydantoins," Indian Journal of Chemistry, Section B: Organic Chemistry including Medicinal Chemistry, 35B(4) (1996) pp. 377-380.
Papadopoulos, E. P., "Reactions of Isocyanates with 1-Cyanothioformanilide," Journal of Organic Chemistry, 44(22) (1979) pp. 3858-3861.

* cited by examiner

DIARYLHYDANTOIN COMPOUNDS

This application is a divisional of U.S. application Ser. No. 12/257,743, filed Oct. 24, 2008, which claims the benefit of U.S. Provisional Application No. 60/996,076, filed Oct. 26, 2007, the specification of which is hereby incorporated by reference.

This invention was made with Government support under Grant No. CA092131 awarded by the National Institutes of Health. The Government has certain rights in this invention.

FIELD OF THE INVENTION

The present invention relates to diarylhydantoin compounds including diarylthiohydantoins, and methods for synthesizing them and using them in the treatment of hormone refractory prostate cancer.

BACKGROUND OF THE INVENTION

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of antiandrogens, the so-called androgen deprivation therapy. Castration lowers the circulating levels of androgens and reduces the activity of androgen receptor (AR). Administration of antiandrogens blocks AR function by competing away androgen binding, therefore, reducing the AR activity. Although initially effective, these treatments quickly fail and the cancer becomes hormone refractory.

Nonsteroidal anti-androgens, such as bicalutamide, have been preferred over steroidal compounds for prostate cancer because they are more selective and have fewer side effects. This class of compounds has been described in patents such as U.S. Pat. No. 4,097,578, U.S. Pat. No. 5,411,981, U.S. Pat. No. 5,705,654, PCT International Applications WO 97/00071 and WO 00/17163, and U.S. Published Patent Application Number 2004/0009969, all of which are hereby incorporated by reference. Bicalutamide (brand name: Casodex) is the most commonly used anti-androgen. While it has an inhibitory effect on AR in hormone sensitive prostate cancer, it fails to suppress AR when cancer becomes hormone refractory.

U.S. Pat. No. 5,434,176 includes broad claims which encompass a very large number of compounds, but synthetic routes are only presented for a small fraction of these compounds and pharmacological data are only presented for two of them, and one skilled in the art could not readily envision other specific compounds. U.S. Pat. No. 5,434,176 is hereby incorporated by reference.

SUMMARY OF THE INVENTION

The invention provides a series of compounds having strong antagonistic activities with minimal agonistic activities against androgen receptor (AR). These compounds inhibit the growth of hormone refractory prostate cancer.

The invention includes a compound having the formula

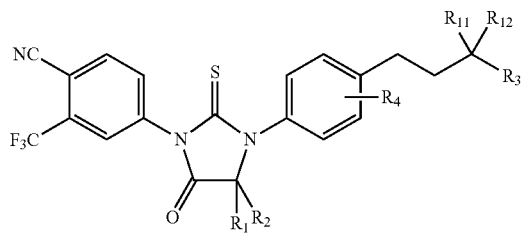

$R_1$ and $R_2$ together can include eight or fewer carbon atoms and can be selected from the group consisting of alkyl, substituted alkyl, and, together with the carbon to which they are linked, a cycloalkyl or substituted cycloalkyl group. $R_3$ can be hydrogen, cyano, formyl,

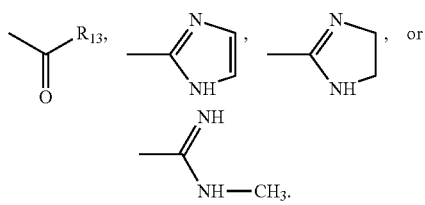

$R_4$ can be hydrogen, F, Cl, Br, or I. $R_{11}$ and $R_{12}$ can be the same or different and are hydrogen or methyl. $R_{13}$ can be hydrogen or —$NR_{14}R_{15}$. $R_{14}$ and $R_{15}$ can be the same or different and are hydrogen or methyl.

For example, $R_1$ and $R_2$ can be independently methyl or, together with the carbon to which they are linked, cyclobutyl or cyclopentyl. For example, $R_{11}$ and $R_{12}$ can be both hydrogen or both methyl. For example, $R_{13}$ can be —NH(CH$_3$) or —N(CH$_3$)$_2$. For example, when $R_4$, $R_{11}$, and $R_{12}$ are each hydrogen and when $R_1$ and $R_2$ together with the carbon to which they are linked are cyclobutyl, then $R_3$ can be other than cyano and

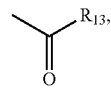

with $R_{13}$ hydrogen, —NH$_2$, —NH(CH$_3$), or —N(CH$_3$)$_2$.

The invention provides a pharmaceutical composition comprising a therapeutically effective amount of a compound according to any of the preceding compounds or a pharmaceutically acceptable salt thereof, and a pharmaceutically acceptable carrier or diluent.

The invention encompasses a method for treating a hyperproliferative disorder comprising administering such a pharmaceutical composition to a subject in need of such treatment, thereby treating the hyperproliferative disorder. The hyperproliferative disorder may be hormone refractory prostate cancer. The dosage may be in the range of from about 0.001 mg per kg body weight per day to about 100 mg per kg body weight per day, about 0.01 mg per kg body weight per day to about 100 mg per kg body weight per day, about 0.1 mg per kg body weight per day to about 10 mg per kg body weight per day, or about 1 mg per kg body weight per day.

The compound may be administered by intravenous injection, by injection into tissue, intraperitoneally, orally, or nasally. The composition may have a form selected from the group consisting of a solution, dispersion, suspension, powder, capsule, tablet, pill, time release capsule, time release tablet, and time release pill.

The invention provides a method of synthesizing a diaryl compound of formula:

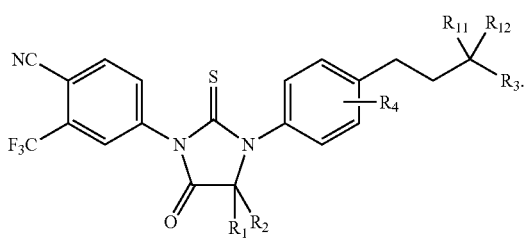

The method includes mixing Compound I

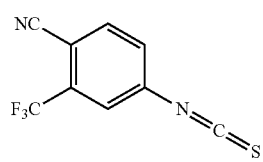
Compound I with Compound II

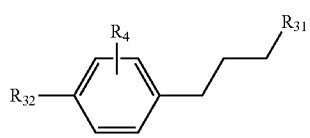
Compound II in a first polar solvent to form a mixture. The method further includes the following: adding a second polar solvent, the same as or different from the first polar solvent, and an aqueous acid to the mixture; refluxing the mixture; cooling the mixture and combining with water; and separating the diaryl compound from the mixture. $R_{31}$ is cyano, carboxy,

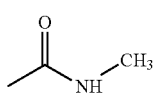

(methylcarbamoyl),

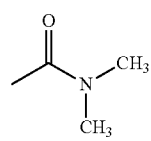

(dimethylcarbamoyl), or

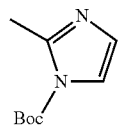

(Boc is t-butoxycarbonyl).

$R_{32}$ is

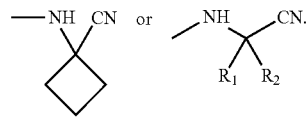

$R_1$ and $R_2$ together include eight or fewer carbon atoms and are alkyl, substituted alkyl, or, together with the carbon to which they are linked, a cycloalkyl or substituted cycloalkyl group. $R_3$ is hydrogen, cyano, formyl,

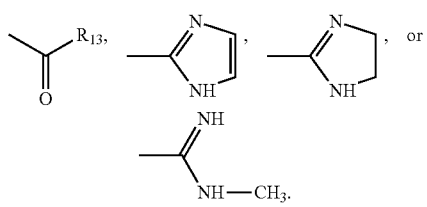

$R_4$ is hydrogen, F, Cl, Br, or I. $R_{11}$ and $R_{12}$ can be the same or different and are hydrogen or methyl. $R_{13}$ is hydrogen or $-NR_{14}R_{15}$. $R_{14}$ and $R_{15}$ can be the same or different and are hydrogen or methyl.

The compounds presented are expected to have substantial androgen receptor antagonist activity and no substantial agonist activity on hormone refractory prostate cancer cells.

The invention encompasses a method comprising providing at least one such compound, measuring inhibition of androgen receptor activity for the compound and determining if the inhibition is above a first predetermined level, measuring stimulation of androgen receptor activity in hormone refractory cancer cells for the compound and determining if the stimulation is below a second predetermined level, and selecting the compound if the inhibition is above the first predetermined level and the stimulation is below the second predetermined level. The predetermined levels may be those of bicalutamide. The step of measuring inhibition may comprise measuring inhibitory concentration (IC50) in an AR response reporter system or a prostate specific antigen secreting system. The step of measuring stimulation may comprise measuring fold induction by increasing concentrations in an AR response reporter system or a prostate specific antigen secreting system. The method of measuring inhibition and/or stimulation may comprise measuring an effect of the compound on tumor growth in an animal.

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

Recently, overexpression of AR has been identified and validated as a cause of hormone refractory prostate cancer. See Chen, C. D., Welsbie, D. S., Tran, C., Baek, S. H., Chen, R., Vessella, R., Rosenfeld, M. G., and Sawyers, C. L., Molecular determinants of resistance to antiandrogen therapy, Nat. Med., 10: 33-39, 2004, which is hereby incorporated by reference. Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explains why castration and anti-androgens fail to prevent prostate cancer progression and reveals unrecognized properties of hormone refractory prostate cancer.

Two weaknesses of current antiandrogens are blamed for the failure to prevent prostate cancer progression from the hormone sensitive stage to the hormone refractory disease and to effectively treat hormone refractory prostate cancer. One is their weak antagonistic activities and the other is their strong agonistic activities when AR is overexpressed in hormone refractory prostate cancer. Better AR inhibitors with more potent antagonistic activities and minimal agonistic activities are needed to delay disease progression and to treat the fatal hormone refractory prostate cancer.

Some new properties of hormone refractory prostate cancer are reported in PCT applications US04/42221 and US05/05529, which are hereby incorporated by reference. PCT International Application US05/05529 presented a methodology for identifying androgen receptor antagonist and agonist characteristics of compounds.

Synthesis of Diarylhydantoin Compounds

The invention provides for synthesis of diarylthiohydantoin compounds having the formula

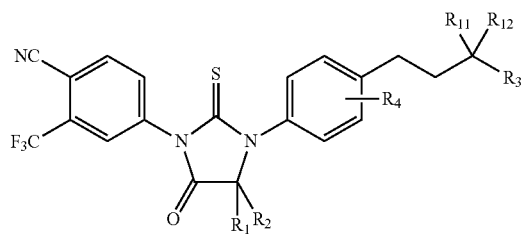

R1 and R2 together can comprise eight or fewer carbon atoms and can be alkyl, substituted alkyl, or, together with the carbon to which they are linked, a cycloalkyl or substituted cycloalkyl group. R3 can be hydrogen, cyano, formyl,

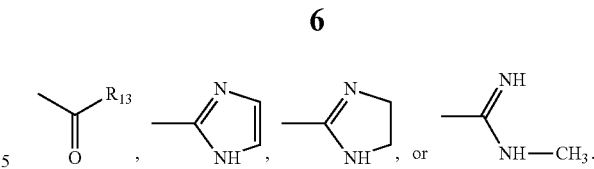

$R_4$ can be hydrogen, F, Cl, Br, and I. $R_{11}$ and $R_{12}$ can be the same or different and can be hydrogen or methyl. $R_{13}$ can be hydrogen or —$NR_{14}R_{15}$. $R_{14}$ and $R_{15}$ can be the same or different and can be hydrogen or methyl.

DEFINITIONS

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which may be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl." For example,

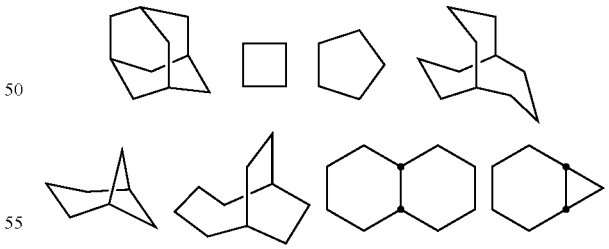

and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heterocyclic" or "heterocycle", as used herein, represents an unsubstituted or substituted stable 5- to 10-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

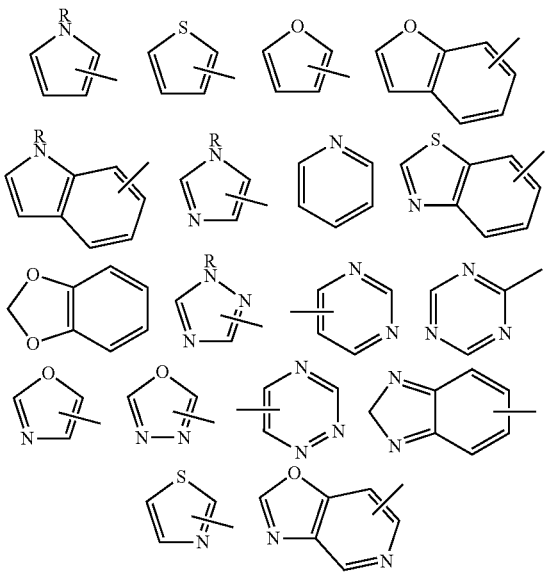

and the like.

Materials were obtained from commercial suppliers and were used without further purification. Air or moisture sensitive reactions were conducted under argon atmosphere using oven-dried glassware and standard syringe/septa techniques. The reactions were monitored with a silica gel TLC plate under UV light (254 nm) followed by visualization with a p-anisaldehyde or ninhydrin staining solution. Column chromatography was performed on silica gel 60. $^1$H NMR spectra were measured at 400 MHz in CDCl$_3$ unless stated otherwise and data were reported as follows in ppm (δ) from the internal standard (TMS, 0.0 ppm): chemical shift (multiplicity, integration, coupling constant in Hz.).

Synthesis of ND-1

4-[4-(t-Butoxycarbonylamino)phenyl]butanoic acid (100)

Di-tert-butyl dicarbonate (0.73 g, 3.35 mmol) was added to a solution of 4-(4-aminophenyl)butyric acid (0.5 g, 2.79 mmol) and sodium hydroxide (0.14 g, 3.35 mmol) in tert-butanol (5 mL) and water (5 mL) at 0° C. The mixture was warmed to room temperature and stirred for 9 h. The mixture was partitioned with diethyl ether (20 mL) and water (20 mL) and then the aqueous layer was acidified to pH 2-3 by 1 N KHSO$_4$ solution. The aqueous mixture extracted with ethyl acetate (3×20 mL) and the organic layer was dried over MgSO$_4$, concentrated to give crude 4-[4-(t-Butoxycarbonylamino)phenyl]butanoic acid (100) (0.73 g, 94%) which was used without further purification.

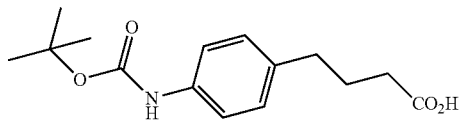 [SMILES: CC(C)(C)OC(=O)Nc1ccc(CCCC(=O)O)cc1]

$^1$H NMR δ 7.26 (d, 2H, J=8.5 Hz), 7.10 (d, 2H, J=8.5 Hz), 6.48 (br s, 1H), 2.62 (t, 2H, J=7.5 Hz), 2.33 (t, 2H, J=7.5 Hz), 1.93 (p, 2H, J=7.5 Hz).

4-[4-(t-Butoxycarbonylamino)phenyl]butanamide (99)

Thionyl chloride (0.22 mL, 3.01 mmol) was added slowly to a solution of 4-[4-(t-Butoxycarbonylamino)phenyl]butanoic acid (100) (0.70 g, 2.51 mmol) in DMF (5 mL) cooled at –5° C. The mixture was stirred for an additional 1 h at –5° C. Excess ammonia (freshly distilled from its aqueous solution) was added to the reaction medium. The second mixture was stirred for an additional 1 h. Ethyl acetate (50 mL) was added to the mixture, which was washed with brine (2×50 mL). The organic layer was dried over MgSO$_4$, concentrated and the residue was purified by silica gel column chromatography (dichloromethane:acetone, 9:1) to give 4-[4-(t-Butoxycarbonylamino)phenyl]butanamide (99) (0.57 g, 82%) as a white solid.

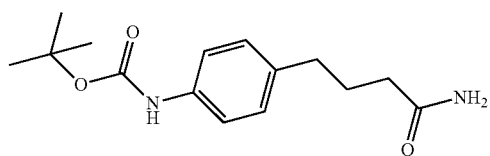 [SMILES: CC(C)(C)OC(=O)Nc1ccc(CCCC(N)=O)cc1]

$^1$H NMR δ 7.26 δ, 2H, J=8.4 Hz), 7.09 (d, 2H, J=8.4 Hz), 6.48 (br s, 1H), 5.47 (br s, 2H), 2.62 (t, 2H, J=7.4 Hz), 2.20 (t, 2H, J=7.4 Hz), 1.94 (p, 2H, J=7.4 Hz), 1.51 (s, 9H).

4-[4-(t-Butoxycarbonylamino)phenyl]butanenitrile (98)

A solution of DMSO (0.13 mL, 1.84 mmol) in dichloromethane (2 mL) was added to a stirred solution of oxalyl chloride (0.12 mL, 1.38 mmol) in dichloromethane (2 mL) at –78° C. After 15 min, a dichloromethane (1 mL) solution of 2 (0.32 g, 1.15 mmol) was added to the reaction mixture. Stirring was continued for 20 min at –78° C., and then triethylamine (0.48 mL, 3.45 mmol) was added. After 30 min, the reaction mixture was warmed to room temperature and then reaction was quenched with saturated aq. NH$_4$Cl solution. The mixture was partitioned with diethyl ether (30 mL) and water (20 mL). The organic layer was dried over MgSO$_4$, concentrated and the residue was purified by silica gel column chromatography (hexane:ethyl acetate, 4:1) to give 4-[4-(t-Butoxycarbonylamino)phenyl]butanenitrile (98) (0.22 g, 73%) as a white solid.

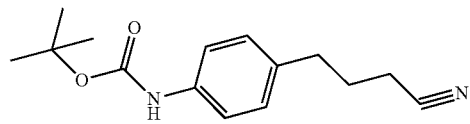 [SMILES: CC(C)(C)OC(=O)Nc1ccc(CCCC#N)cc1]

$^1$H NMR δ 7.30 (d, 2H, J=8.4 Hz), 6.10 (d, 2H, J=8.4 Hz), 6.42 (br s, 1H), 2.73 (t, 2H, J=7.3 Hz), 2.30 (t, 2H, J=7.3 Hz), 1.95 (p, 2H, J=7.3 Hz), 1.52 (s, 9H).

4-(4-Aminophenyl)butanenitrile (97)

A 0.25 M solution of trifluoroacetic acid in dichloromethane (5 mL, 1.25 mmol) was added to 4-[4-(t-Butoxycarbonylamino)phenyl]butanenitrile (98) (0.22 g, 0.85 mmol). After 30 min, reaction was quenched with 1 N NaOH solution. The mixture was partitioned with ethyl acetate (30 mL) and water (20 mL). The organic layer was dried over MgSO$_4$, concentrated to give 4-(4-Aminophenyl)butanenitrile (97) (0.16 g, 99%) which was used without further purification.

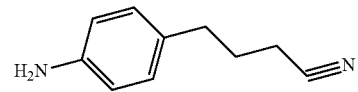 [SMILES: N#CCCCc1ccc(N)cc1]

$^1$H NMR δ 6.97 (d, 2H, J=8.5 Hz), 6.64 (d, 2H, J=8.5 Hz), 3.59 (br s, 2H), 2.67 (t, 2H, J=7.3 Hz), 2.29 (t, 2H, J=7.3 Hz), 1.92 (p, 2H, J=7.3 Hz).

4-Isothiocyanato-2-trifluoromethylbenzonitrile (96)

4-Amino-2-trifluoromethylbenzonitrile (2.23 g, 12 mmol) was added portionwise over 15 min into a well-stirred heterogeneous mixture of thiophosgene (1 mL, 13 mmol) in water (22 mL) at room temperature. Stirring was continued for an additional 1 h. The reaction medium was extracted with chloroform (3×15 mL). The combined organic phase was dried over MgSO$_4$ and evaporated to dryness under reduced pressure to yield desired product 4-Isothiocyanato-2-trifluoromethylbenzonitrile (96) (2.72 g, 11.9 mmol, 99%) as brownish solid and was used without further purification.

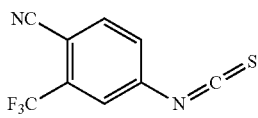 [SMILES: N#Cc1ccc(N=C=S)cc1C(F)(F)F]

$^1$H NMR δ 7.84 (d, 1H, J=8.3 Hz), 7.59 (d, 1H, J=2.1 Hz), 7.49 (dd, 1H, J=8.3, 2.1 Hz).

4-[4-(1-Cyanodimethylamino)phenyl]butanenitrile (95)

A mixture of 4-(4-Aminophenyl)butanenitrile (97) (50 mg, 0.26 mmol), acetone cyanohydrin (0.15 mL, 1.58 mmol) was heated to 80° C. and stirred for 12 h. To the medium was added ethyl acetate (20 mL) and then washed with water (2×20 mL). The organic layer was dried over MgSO$_4$, concentrated and the residue was purified by silica gel column chromatography (hexane:ethyl acetate, 1:1) to give 4-[4-(1-Cyanodimethylamino)phenyl]butanenitrile (95) (52 mg, 87%) as a white solid.

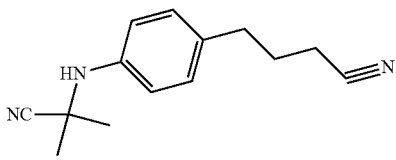 [SMILES: CC(C)(C#N)Nc1ccc(CCCC#N)cc1]

$^1$H NMR δ 7.07 (d, 2H, J=8.3 Hz), 6.87 (d, 2H, J=8.3 Hz), 3.68 (br s, 1H), 2.70 (t, 2H, J=7.3 Hz), 2.31 (t, 2H, J=7.3 Hz), 1.94 (p, 2H, J=7.3 Hz), 1.69 (s, 6H).

4-(3-(4-(3-Cyanopropyl)phenyl)-4,4-dimethyl-5-oxo-2-thioxo-imidazolidin-1-yl)-2-(trifluoromethyl)benzonitrile (94) [ND-1]

A mixture of 4-Isothiocyanato-2-trifluoromethylbenzonitrile (96) (32 mg, 0.14 mmol) and 4-[4-(1-Cyanodimethylamino)phenyl]butanenitrile (95) (16 mg, 0.07 mmol) in DMF (1 mL) was heated under microwave irradiation at 80° C. for 6 h. To this mixture was added methanol (10 mL) and aq. 1 N HCl (3 mL). The second mixture was refluxed for 1.5 h. After being cooled to room temperature, the reaction mixture was poured into cold water (20 mL) and extracted with ethyl acetate (30 mL). The organic layer was dried over MgSO$_4$, concentrated and the residue was purified by silica gel column chromatography (hexane:ethyl acetate, 2:1) to give 4-(3-(4-(3-Cyanopropyl)phenyl)-4,4-dimethyl-5-oxo-2-thioxo-imidazolidin-1-yl)-2-(trifluoromethyl)benzonitrile (94) [ND-1](20 mg, 62%) as a white solid.

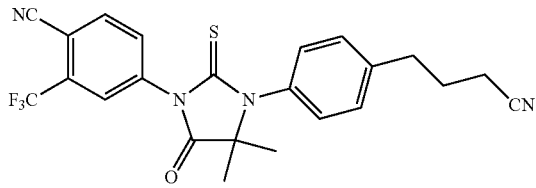 [SMILES: CC1(C)C(=O)N(c2ccc(C#N)c(C(F)(F)F)c2)C(=S)N1c1ccc(CCCC#N)cc1]

$^1$H NMR δ 7.98 (d, 1H, J=8.3 Hz), 7.97 (d, 1H, J=1.8 Hz), 7.85 (dd, 1H, J=8.3, 1.8 Hz), 7.37 (d, 2H, J=8.3 Hz), 7.25 (d, 2H, J=8.3 Hz), 2.87 (t, 2H, J=7.0 Hz), 2.40 (t, 2H, J=7.0 Hz), 2.05 (p, 2H, J=7.0 Hz), 1.59 (s, 6H).

Synthesis of ND-2

4-[4-(1-Cyanocyclopentyl amino)phenyl]butanenitrile (93)

A mixture of 4-(4-Aminophenyl)butanenitrile (97) (52 mg, 0.27 mmol), cyclopentanone (0.07 mL, 0.55 mmol) and TMSCN (0.05 mL, 0.55 mmol) was heated to 80° C. and stirred for 13 h. To the medium was added ethyl acetate (2×20 mL) and then washed with water (2×20 mL). The organic layer was dried over MgSO$_4$, concentrated and the residue was purified with silica gel column chromatography (hexane:ethyl acetate, 1:1) to give 4-[4-(1-Cyanocyclopentyl amino)phenyl]butanenitrile (93) (70 mg, quant.) as a white solid.

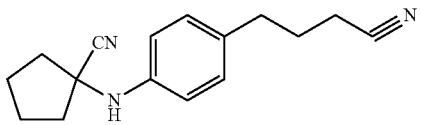 [SMILES: N#CCCCc1ccc(NC2(C#N)CCCC2)cc1]

$^1$H NMR δ 7.06 (d, 2H, J=8.3 Hz), 6.78 (d, 2H, J=8.3 Hz), 3.80 (br s, 1H), 2.70 (t, 2H, J=7.3 Hz), 2.34-2.42 (m, 2H), 2.31 (t, 2H, J=7.3 Hz), 2.09-2.18 (m, 2H), 1.94 (p, 2H, J=7.3 Hz), 1.86-1.91 (m, 4H).

4-(1-(4-(3-Cyanopropyl)phenyl)-4-oxo-2-thioxo-1,3-diazaspiro[4.4]non-3-yl)-2-trifluoromethylbenzonitrile (92) [ND-2]

A mixture of 4-Isothiocyanato-2-trifluoromethylbenzonitrile (96) (36 mg, 0.16 mmol) and 4-[4-(1-Cyanocyclopentyl amino)phenyl]butanenitrile (93) (20 mg, 0.08 mmol) in DMF (1 mL) was heated under microwave irradiation at 80° C. for 6 h. To this mixture was added methanol (10 mL) and aq. 1 N HCl (3 mL). The second mixture was refluxed for 1.5 h. After being cooled to room temperature, the reaction mixture was poured into cold water (20 mL) and extracted with ethyl acetate (30 mL). The organic layer was dried over MgSO$_4$, concentrated and the residue was purified by silica gel column chromatography (hexane:ethyl acetate, 2:1) to give 4-(1-(4-(3-Cyanopropyl)phenyl)-4-oxo-2-thioxo-1,3-diazaspiro[4.4]non-3-yl)-2-trifluoromethylbenzonitrile (92) [ND-2]

(25 mg, 65%) as a white solid. $^1$H NMR δ 7.98 (d, 1H, J=1.8 Hz), 7.97 (d, 1H, J=8.3 Hz), 7.86 (dd, 1H, J=8.3, 1.8 Hz), 7.37 (d, 2H, J=8.3 Hz), 7.27 (d, 2H, J=8.3 Hz), 2.87 (t, 2H, J=7.3 Hz), 2.40 (t, 2H, J=7.3 Hz), 2.28-2.35 (m, 2H), 2.14-2.23 (m, 2H), 2.05 (p, 2H, J=7.3 Hz), 1.85-1.92 (m, 2H), 1.48-1.55 (m, 2H).

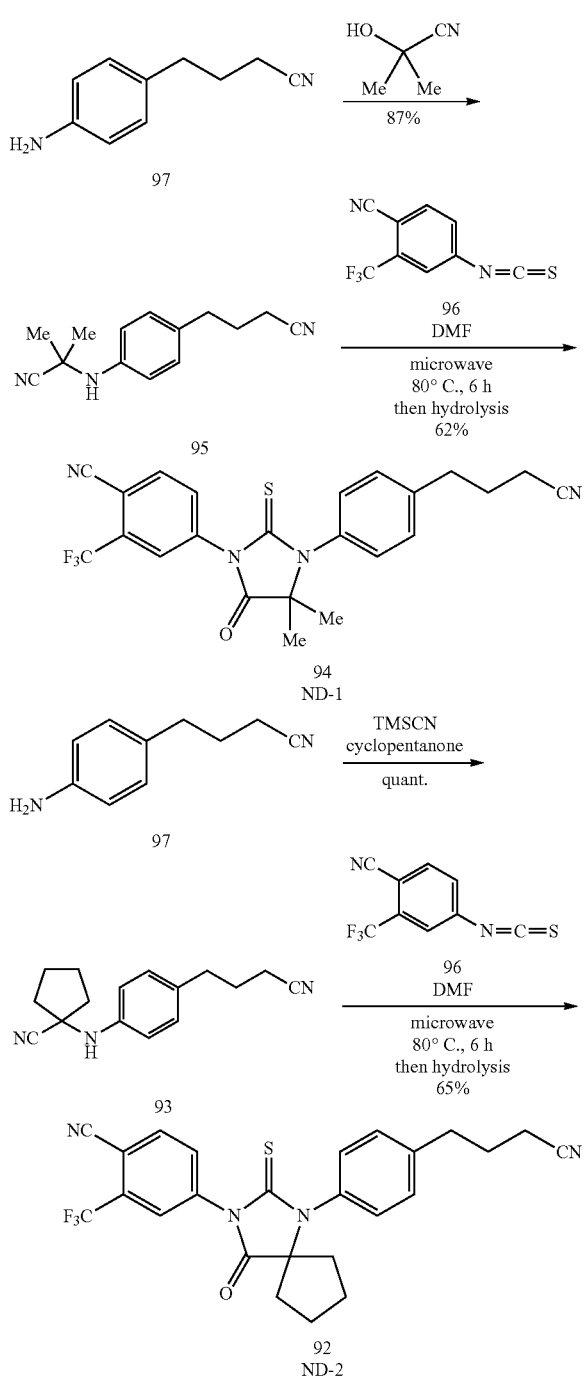

94
ND-1

93

92
ND-2

Synthesis of ND-14

4-(3-(4-(3-Cyanopropyl)-3-fluorophenyl)-4,4-dimethyl-5-oxo-2-thioxo-imidazolidin-1-yl)-2-(trifluoromethyl)benzonitrile (103)

4-(3-(4-(3-Cyanopropyl)-3-fluorophenyl)-4,4-dimethyl-5-oxo-2-thioxo-imidazolidin-1-yl)-2-(trifluoromethyl)benzonitrile (103) [ND-14] can be synthesized in a manner similar as to that for synthesizing (92) [ND-2]. A mixture of 4-Isothiocyanato-2-trifluoromethylbenzonitrile (96) and 4-(4-(2-cyanopropan-2-ylamino)-2-fluorophenyl)butanenitrile (101) in solvent, for example, in DMF, is heated under microwave irradiation at 80° C. for 6 h.

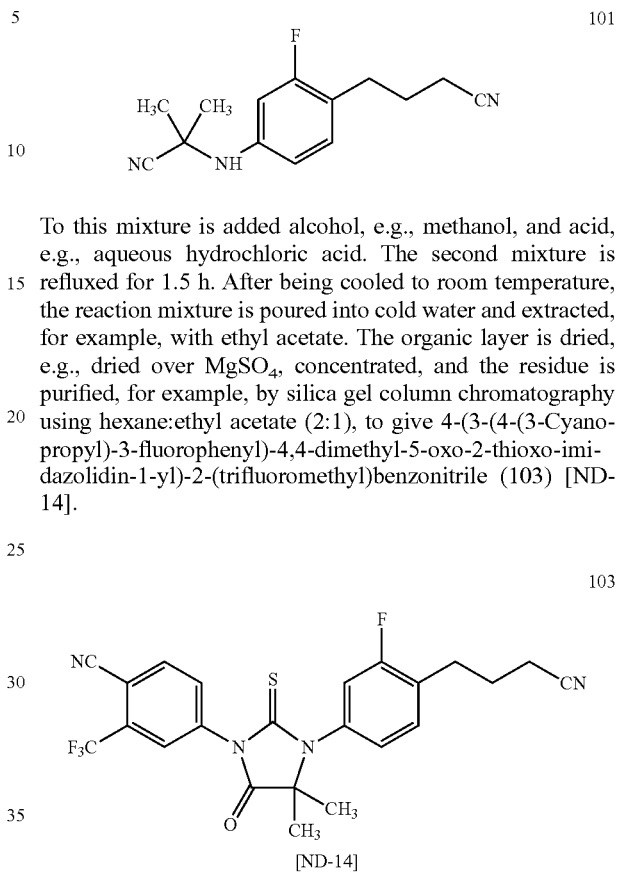

101

To this mixture is added alcohol, e.g., methanol, and acid, e.g., aqueous hydrochloric acid. The second mixture is refluxed for 1.5 h. After being cooled to room temperature, the reaction mixture is poured into cold water and extracted, for example, with ethyl acetate. The organic layer is dried, e.g., dried over MgSO$_4$, concentrated, and the residue is purified, for example, by silica gel column chromatography using hexane:ethyl acetate (2:1), to give 4-(3-(4-(3-Cyanopropyl)-3-fluorophenyl)-4,4-dimethyl-5-oxo-2-thioxo-imidazolidin-1-yl)-2-(trifluoromethyl)benzonitrile (103) [ND-14].

103

[ND-14]

Synthesis of ND-3

4-[4-(1-Cyanocyclobutylamino)-phenyl]-butyric acid (91)

Trimethylsilyl cyanide (0.50 g, 5 mmol) was added dropwise to a mixture of 4-(4-aminophenyl)-butyric acid (0.537 g, 3 mmol), cyclobutanone (0.35 g, 5 mmol) and sodium sulfate (1 g) in 1,4-dioxane (10 ml). The mixture was stirred for 15 hours. After filtration to eliminate sodium sulfate, the medium was concentrated under vacuum to obtain a brown liquid which was subjected to chromatography (dichloromethane:acetone, 50:50) to yield 4-[4-(1-Cyanocyclobutylamino)-phenyl]-butyric acid (91) (0.665 g, 2.58 mmol, 86%) as a yellowish solid.

4-{4-[7-(4-cyano-3-trifluoromethylphenyl)-8-oxo-6-thioxo-5,7-diazaspiro[3.4]oct-5-yl]-phenyl}-butyric acid methyl ester (90) [ND-4]

A mixture of 4-isothiocyanato-2-trifluoromethylbenzonitrile (96) (0.547 g, 2.4 mmol) and 4-[4-(1-Cyanocyclobutylamino)-phenyl]-butyric acid (91) (0.342 g, 1.5 mmol) in dry DMF (2 ml) was stirred at room temperature for 15 hours. To this mixture were added methanol (10 ml) and HCl aq. (5 ml, 2M). The second mixture was refluxed for 3 h. After being cooled to room temperature, the reaction mixture was poured into cold water (10 ml) and extracted with ethyl acetate (3×30 ml). The organic layer was dried over MgSO$_4$, concentrated and chromatographed (dichloromethane) to yield 4-{4-[7-(4-cyano-3-trifluoromethylphenyl)-8-oxo-6-thioxo-5,7-diazaspiro[3.4]oct-5-yl]-phenyl}-butyric acid methyl ester (90) [ND-4](0.594 g, 1.18 mmol, 79%) as a white powder.

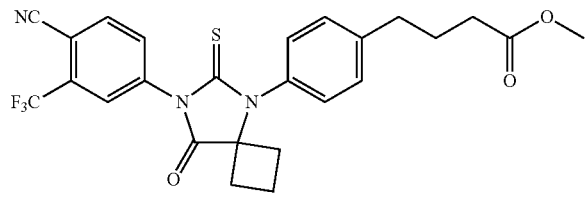 [SMILES: COC(=O)CCCc1ccc(N2C(=S)N(c3ccc(C#N)c(C(F)(F)F)c3)C(=O)C23CCC3)cc1]

$^1$H NMR (CDCl$_3$, 400 MHz) δ 1.60-1.70 (m, 1H), 1.98-2.07 (m, 2H), 2.14-2.26 (m, 1H), 2.40 (t, J=7.4 Hz, 2H), 2.52-2.60 (m, 2H), 2.62-2.68 (m, 2H), 2.74 (t, J=7.4 Hz, 2H), 3.68 (s, 3H), 7.22 (d, J=8.2 Hz, 2H), 7.38 (d, J=8.2 Hz, 2H), 7.86 (dd, J$_1$=8.3 Hz, J$_2$=1.8 Hz, 1H), 7.95 (d, J=8.3 Hz, 1H), 7.98 (d, J=1.8 Hz, 1H); $^{13}$C NMR (CDCl$_3$, 100 MHz) δ 13.7, 26.1, 31.4, 33.5, 34.8, 51.7, 67.5, 109.9, 114.9, 121.9 (q, J=272.7 Hz), 127.1 (q, J=4.7 Hz), 129.7, 130.1, 132.3, 133.0, 133.3 (q, J=33.2 Hz), 135.2, 137.2, 143.5, 173.8, 175.0, 179.9.

4-{4-[7-(4-cyano-3-trifluoromethylphenyl)-8-oxo-6-thioxo-5,7-diaza-spiro[3.4]oct-5-yl]-phenyl}-butyric acid (89) [ND-5]

A mixture of 4-{4-[7-(4-cyano-3-trifluoromethylphenyl)-8-oxo-6-thioxo-5,7-diazaspiro[3.4]oct-5-yl]-phenyl}-butyric acid methyl ester (90) [ND-4](0.501 g, 1 mmol) in methanol (10 ml) and solution of sodium hydroxide (10 ml, 2M) was stirred at room temperature for 5 hours. The methanol was evaporated. The residue was adjusted to pH=5 by HCl aq. (2M) and then, the medium was extracted with ethyl acetate (3×50 ml). The organic layer was dried over MgSO$_4$ and concentrated to dryness to obtain 4-{4-[7-(4-cyano-3-trifluoromethylphenyl)-8-oxo-6-thioxo-5,7-diaza-spiro[3.4]oct-5-yl]-phenyl}-butyric acid (89) [ND-5](0.482 g, 0.99 mmol, 99%), the structure of which is illustrated in Formula 89.

Formula 89

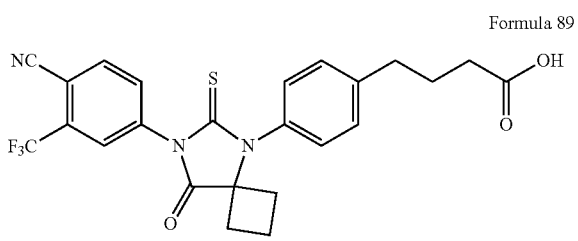 [SMILES: N#Cc1ccc(N2C(=O)C3(CCC3)N(c3ccc(CCCC(=O)O)cc3)C2=S)cc1C(F)(F)F]

$^1$H NMR (CDCl$_3$, 400 MHz) δ 1.60-1.70 (m, 1H), 1.98-2.07 (m, 2H), 2.14-2.26 (m, 1H), 2.45 (t, J=7.3 Hz, 2H), 2.51-2.59 (m, 2H), 2.62-2.68 (m, 2H), 2.77 (t, J=7.3 Hz, 2H), 7.23 (d, J=8.1 Hz, 2H), 7.40 (d, J=8.1 Hz, 2H), 7.85 (dd, J=8.3, 1.8 Hz, 1H), 7.95 (d, J=8.3 Hz, 1H), 7.97 (d, J=1.8 Hz, 1H); $^{13}$C NMR (CDCl$_3$, 100 MHz) δ 13.7, 25.9, 31.4, 33.4, 34.7, 67.5, 109.9, 114.9, 121.9 (q, J=272.6 Hz), 127.1 (q, J=4.7 Hz), 129.8, 130.1, 132.3, 133.0, 133.4 (q, J=33.1 Hz), 135.2, 137.2, 143.3, 174.9, 178.9, 179.9.

42-5) 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6]

To a suspension of 4-{4-[7-(4-cyano-3-trifluoromethylphenyl)-8-oxo-6-thioxo-5,7-diaza-spiro[3.4]oct-5-yl]-phenyl}-butyric acid (89) (0.097 g, 0.2 mmol) in THF (10 ml) at −5° C. was added thionyl chloride (0.019 ml, 0.26 mmol). The medium was stirred at −5° C. for one hour. Then methylamine was bubbled into the mixture at −5° C. for 30 minutes. The medium was filtered. The filtrate was concentrated and chromatographed (dichloromethane:acetone, 75:25) to yield 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6](0.095 g, 0.19 mmol, 95%) as an off-white powder.

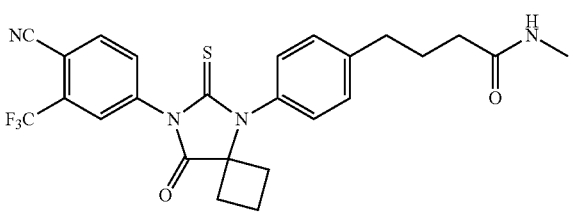 [SMILES: CNC(=O)CCCc1ccc(N2C(=S)N(c3ccc(C#N)c(C(F)(F)F)c3)C(=O)C23CCC3)cc1]

$^1$H NMR (CDCl$_3$, 400 MHz) δ 1.52-1.64 (m, 1H), 1.94-2.01 (m, 2H), 2.10-2.17 (m, 1H), 2.20 (t, J=7.3 Hz, 2H), 2.46-2.62 (m, 4H), 2.69 (t, J=7.3 Hz, 2H), 2.73 (d, J=4.7 Hz, 3H), 6.09 (bs, 1H), 7.16 (d, J=8.2 Hz, 2H), 7.33 (d, J=8.2 Hz, 2H), 7.82 (dd, J=8.3 Hz, J$_2$=1.8 Hz, 1H), 7.91 (d, J=8.3 Hz, 1H), 7.94 (d, J=1.8 Hz, 1H); $^{13}$C NMR (CDCl$_3$, 100 MHz) δ 13.7, 26.2, 26.8, 31.4, 35.0, 35.7, 67.5, 109.7, 114.9, 121.9 (q, J=272.7 Hz), 127.1 (q, J=4.7 Hz), 129.7, 130.0, 132.3, 133.8, 133.3 (q, J=33.2 Hz), 135.2, 137.3, 143.7, 173.3, 174.9, 179.8.

4-(4-(7-(4-Cyano-3-(trifluoromethyl)phenyl)-8-oxo-6-thioxo-5,7-diazaspiro[3.4]oct-an-5-yl)phenyl)-N-methylbutanimidamide (87) [ND-3]

To a solution of 4-{4-[7-(4-Cyano-3-trifluoromethylphenyl)-8-oxo-6-thioxo-5,7-diaza-spiro[3.4]oct-5-yl]-phenyl}-N-methyl-butyramide (88) [ND-6](4.0 mg, 0.008 mmol) and pyridine (1.94 µL, 0.02 mmol) in dichloromethane (3 mL) at −40° C. was slowly added triflic anhydride (Tf$_2$O, 1.75 µL, 0.01 mmol). The mixture was allowed to warm to 0° C. over 3 h. The solution was then cooled to −40° C. and ammonia was introduced by bubbling. The reaction was then warmed to room temperature and stirred overnight. Without aqueous work up, flash chromatography using 10% methanol in ethyl acetate afforded 4-(4-(7-(4-Cyano-3-(trifluoromethyl)phenyl)-8-oxo-6-thioxo-5,7-diazaspiro[3.4]oct-an-5-yl)phenyl)-N-methylbutanimidamide (87) [ND-3](2.9 mg, 72%) of as a colorless oil: 1H NMR (CD$_3$CN) δ 8.10 (d, 1H, J=8.2 Hz), 8.04 (s, 1H), 7.92 (d, 1H, J=8.2 Hz), 7.49 (br s, 2H), 7.43 (d, 2H, J=8.3 Hz), 7.30 (d, 2H, J=8.3 Hz), 3.26 (d, 3H, J=5.4 Hz), 2.77 (t, 2H, J=8.0 Hz), 2.56-2.65 (m, 2H), 2.52 (t, 2H, J=7.7 Hz), 2.42-2.52 (m, 2H), 1.95-2.12 (m, 3H), 1.47-1.62 (m, 1H).

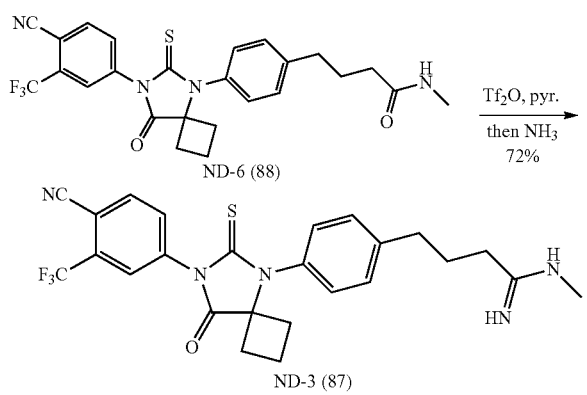

Synthesis of ND-7 and ND-8

Dimethyl 2-(2-fluoro-4-nitrophenyl)malonate (86)

To a suspension of sodium hydride (NaH, 60%, 0.40 g, 10.0 mmol) in dry DMF (10 mL) under ice cooling was added dimethyl malonate (1.04 mL, 9.1 mmol) dropwise followed by a solution of 1-bromo-2-fluoro-4-nitrobenzene (1.00 g, 4.55 mmol) in dry DMF (3 mL) under an argon atmosphere. The resulting mixture was stirred at 70° C. overnight and then allowed to cool to 21° C. The reaction mixture was quenched with saturated NH$_4$Cl and extracted with ethyl acetate (2×50 mL). The organic layer was dried over MgSO$_4$, concentrated and the residue was purified with silica gel column chromatography (hexane:ethyl acetate, 2:1) to give Dimethyl 2-(2-fluoro-4-nitrophenyl)malonate (86) (0.90 g, 73%) as a light yellowish solid: 1H NMR δ 8.07 (dd, 1H, J=8.6, 2.2 Hz), 7.98 (dd, 1H, J=9.3, 2.2 Hz), 7.74 (dd, 1H, J=8.6, 7.1 Hz), 5.08 (s, 1H), 3.81 (s, 6H).

Trimethyl 1-(2-fluoro-4-nitrophenyl)propane-1,1,3-tricarboxylate (85)

To a solution of the nitro diester, Dimethyl 2-(2-fluoro-4-nitrophenyl)malonate (86) (0.44 g, 1.62 mmol) and methyl acrylate (0.22 mL, 2.43 mmol) in absolute methanol (5 mL) was added a catalytic amount of sodium methoxide at 21° C. under argon. The reaction mixture was stirred for 40 h at the same temperature and then diluted with dichloromethane (50 mL). The resulting mixture was washed with water, brine and dried. The residue obtained upon evaporation of the solvents was purified on a silica gel (hexane:ethyl acetate, 8:1) to give Trimethyl 1-(2-fluoro-4-nitrophenyl)propane-1,1,3-tricarboxylate (85) (0.49 g, 85%): 1H NMR δ 8.04 (dd, 1H, J=8.7, 2.3 Hz), 7.95 (dd, 1H, J=10.9, 2.3 Hz), 7.57 (dd, 1H, J=8.7, 7.5 Hz), 3.81 (s, 6H), 3.62 (s, 3H), 2.64-2.69 (m, 2H), 2.35-2.40 (m, 2H).

Methyl 4-(2-fluoro-4-nitrophenyl)butanoate (84)

A solution of compound Trimethyl 1-(2-fluoro-4-nitrophenyl)propane-1,1,3-tricarboxylate (85) (0.23 g, 0.63 mmol), sodium chloride (0.11 g, 1.90 mmol) and water (0.15 mL) in distilled dimethylsulfoxide (4 mL) was heated to 155° C. overnight. The reaction mixture was allowed to cool to 21° C. and then worked up by adding water and extracting with ethyl acetate (2×50 mL). The organic layer was dried over MgSO$_4$, concentrated and the residue was purified with silica gel column chromatography (hexane:ethyl acetate, 8:1) to give desired Methyl 4-(2-fluoro-4-nitrophenyl)butanoate (84) (69 mg, 45%) and dimethyl 2-(2-fluoro-4-nitrophenyl)pentanedioate (83) (72 mg, 38%): 1H NMR of (10) δ 8.04 (dd, 1H, J=8.5, 2.2 Hz), 7.95 (dd, 1H, J=9.5, 2.2 Hz), 7.53 (dd, 1H, J=8.5, 7.1 Hz), 4.08 (t, 1H, J=7.6 Hz), 3.71 (s, 3H), 3.66 (s, 3H), 2.43-2.52 (m, 1H), 2.31-2.35 (m, 2H), 2.06-2.14 (m, 1H); 1H NMR of (84) δ 7.98 (dd, 1H, J=8.4, 2.2 Hz), 7.90 (dd, 1H, J=9.5, 2.2 Hz), 7.38 (dd, 1H, J=8.4, 7.3 Hz), 3.68 (s, 3H), 2.79 (t, 2H, J=7.7 Hz), 2.38 (t, 2H, J=7.3 Hz), 1.94-2.02 (m, 2H).

4-(2-Fluoro-4-nitrophenyl)butanoic acid (82)

To a solution of Methyl 4-(2-fluoro-4-nitrophenyl)butanoate (84) (43 mg, 0.18 mmol) in methanol (1 mL) and water (3 mL) was added sodium hydroxide (0.18 g, 4.50 mmol). The reaction mixture was stirred at 21° C. overnight. The reaction mixture was quenched with 1 N HCl solution and extracted with ethyl acetate (2×30 mL). The organic layer was dried over MgSO$_4$, concentrated to give 4-(2-Fluoro-4-nitrophenyl)butanoic acid (82) (40 mg, 98%) and the residue was used without further purification.

4-(2-Fluoro-4-nitrophenyl)-N-methylbutanamide (81)

Thionyl chloride (0.01 mL, 0.11 mmol) was added slowly to a solution of 4-(2-Fluoro-4-nitrophenyl)butanoic acid (82) (20 mg, 0.09 mmol) in DMF (3 mL) cooled at −5° C. The mixture was stirred for an additional 1 h at −5° C. Excess methylamine (freshly distilled from its 40% aqueous solution) was added to the reaction medium. The second mixture was stirred for an additional 1 h. Ethyl acetate (30 mL) was added to the mixture, which was washed with brine (2×30 mL). The organic layer was dried over MgSO$_4$, and concentrated to yield 4-(2-Fluoro-4-nitrophenyl)-N-methylbutanamide (81) (18 mg, 85%): 1H NMR δ 7.97 (dd, 1H, J=8.4, 2.2 Hz), 7.89 (dd, 1H, J=9.5, 2.2 Hz), 7.40 (dd, 1H, J=8.4, 7.3 Hz), 5.44 (br s, 1H), 2.81 (d, 3H, J=4.9 Hz), 2.79 (t, 2H, J=7.6 Hz), 2.22 (t, 2H, J=7.3 Hz), 1.96-2.04 (m, 2H).

4-(4-Amino-2-fluorophenyl)-N-methylbutanamide (80)

A solution of compound 4-(2-Fluoro-4-nitrophenyl)-N-methylbutanamide (81) (18 mg, 0.07 mmol), Fe (30 mg, 0.52 mmol) and AcOH (1 mL) in ethyl acetate (3 mL) was heated under reflux for 2 h. The reaction mixture was allowed to cool to 21° C. and then filtered.

The organic layer was concentrated and the residue was purified with silica gel column chromatography (dichloromethane:acetone, 9:1) to give desired 4-(4-Amino-2-fluorophenyl)-N-methylbutanamide (80) (14 mg, 86%): 1H NMR δ 6.92 (dd, 1H, J=8.3, 8.2 Hz), 6.39 (dd, 1H, J=8.3, 2.0 Hz), 6.33 (dd, 1H, J=13.3, 2.0 Hz), 5.48 (br s, 1H), 3.69 (br s, 2H), 2.79 (d, 3H, J=4.8 Hz), 2.55 (t, 2H, J=7.4 Hz), 2.16 (t, 2H, J=7.5 Hz), 1.85-1.94 (m, 2H).

4-(4-(1-Cyanocyclobutylamino)-2-fluorophenyl)-N-methylbutanamide (79)

A mixture of 4-(4-Amino-2-fluorophenyl)-N-methylbutanamide (80) (8 mg, 0.04 mmol), cyclobutanone (5 mg, 0.08 mmol) and trimethylsilyl cyanide (TMSCN, 8 mg, 0.08 mmol) was heated to 80° C. and stirred for 15 h. To the medium was added ethyl acetate (2×20 mL) and then washed with water (2×20 mL). The organic layer was dried over MgSO$_4$ and concentrated and the residue was purified with silica gel column chromatography (dichloromethane:acetone, 9:1) to give 4-(4-(1-Cyanocyclobutylamino)-2-fluorophenyl)-N-methylbutanamide (79) (10 mg, 92%).

4-(4-(7-(4-Cyano-3-(trifluoromethyl)phenyl)-8-oxo-6-thioxo-5,7-diazaspiro[3.4]oct-an-5-yl)-2-fluorophenyl)-N-methylbutanamide (78) [ND-7]

A mixture of 4-(4-(1-Cyanocyclobutylamino)-2-fluorophenyl)-N-methylbutanamide (79) (7 mg, 0.02 mmol) and 4-isothiocyanato-2-trifluoromethylbenzonitrile (96) (12 mg, 0.05 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL) and extracted with ethyl acetate (30 mL). The organic layer was dried over MgSO$_4$, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]oct-an-5-yl)-2-fluorophenyl)-N-methylbutanamide (78) [ND-7](8 mg, 62%) as a pale yellowish solid: $^1$H NMR δ 7.98 (d, 1H, J=8.2 Hz), 7.97 (d, 1H, J=2.0 Hz), 7.84 (dd, 1H, J=8.2, 2.0 Hz), 7.43 (dd, 1H, J=8.0, 8.0 Hz), 7.06 (dd, 1H, J=8.0, 2.0 Hz), 7.02 (dd, 1H, J=9.7, 2.0 Hz), 2.83 (d, 3H, J=4.8 Hz), 2.78 (t, 2H, J=7.7 Hz), 2.63-2.71 (m, 2H), 2.51-2.62 (m, 2H), 2.27 (t, 2H, J=7.3 Hz), 2.18-2.27 (m, 1H), 2.00-2.09 (m, 2H), 1.66-1.76 (m, 1H); $^{13}$C NMR δ 179.9, 174.7, 172.8, 161.2 (d, J=247 Hz), 137.0, 135.2, 134.1 (d, J=9.6 Hz), 133.6 (q, J=33.7 Hz), 132.1, 131.9 (d, J=5.6 Hz), 130.8 (d, J=15.2 Hz), 127.1, 125.7 (d, J=3.9 Hz), 121.9 (q, J=272 Hz), 117.3 (d, J=22.3 Hz), 114.8, 110.0, 67.4, 35.8, 31.5, 28.3, 26.4, 25.6, 13.7.

4-(2-Fluoro-4-nitrophenyl)-N,N-dimethylbutanamide (77)

Thionyl chloride (0.01 mL, 0.11 mmol) was added slowly to a solution of 4-(2-Fluoro-4-nitrophenyl)butanoic acid (82) (18 mg, 0.08 mmol) in DMF (3 mL) cooled at −5° C. The mixture was stirred for an additional 1 h at −5° C. Excess dimethylamine (freshly distilled from its 40% aqueous solution) was added to the reaction medium. The second mixture was stirred for an additional 1 h. Ethyl acetate (30 mL) was added to the mixture, which was washed with brine (2×30 mL). The organic layer was dried over MgSO$_4$, and concentrated to yield 4-(2-Fluoro-4-nitrophenyl)-N,N-dimethylbutanamide (77) (18 mg, 87%): $^1$H NMR δ 7.98 (dd, 1H, J=8.3, 2.1 Hz), 7.89 (dd, 1H, J=9.5, 2.1 Hz), 7.42 (dd, 1H, J=8.3, 7.4 Hz), 2.98 (s, 3H), 2.95 (s, 3H), 2.81 (t, 2H, J=7.6 Hz), 2.36 (t, 2H, J=7.2 Hz), 1.96-2.04 (m, 2H).

4-(4-Amino-2-fluorophenyl)-N,N-dimethylbutanamide (76)

A solution of compound 4-(2-Fluoro-4-nitrophenyl)-N,N-dimethylbutanamide (77) (15 mg, 0.06 mmol), Fe (20 mg, 0.37 mmol) and acetic acid (1 mL) in ethyl acetate (3 mL) was heated under reflux for 2 h. The reaction mixture was allowed to cool to 21° C. and then filtered. The organic layer was concentrated and the residue was purified with silica gel column chromatography (dichloromethane:acetone, 9:1) to give desired 4-(4-Amino-2-fluorophenyl)-N,N-dimethylbutanamide (76) (12 mg, 87%): $^1$H NMR δ 6.95 (dd, 1H, J=8.3, 8.2 Hz), 6.40 (dd, 1H, J=8.3, 2.2 Hz), 6.35 (dd, 1H, J=11.6, 2.2 Hz), 3.66 (br s, 2H), 2.95 (s, 3H), 2.93 (s, 3H), 2.58 (t, 2H, J=7.4 Hz), 2.30 (t, 2H, J=7.6 Hz), 1.85-1.95 (m, 2H).

4-(4-(2-Cyanopropan-2-ylamino)-2-fluorophenyl)-N,N-dimethylbutanamide (75)

A mixture of 4-(4-Amino-2-fluorophenyl)-N,N-dimethylbutanamide (76) (10 mg, 0.05 mmol), cyclobutanone (6 mg, 0.09 mmol) and trimethylsilyl cyanide (TMSCN, 9 mg, 0.09 mmol) was heated to 80° C. and stirred for 15 h. To the medium was added ethyl acetate (2×20 mL) and then washed with water (2×20 mL). The organic layer was dried over MgSO$_4$ and concentrated and the residue was purified with silica gel column chromatography (dichloromethane:acetone, 9:1) to give 4-(4-(2-Cyanopropan-2-ylamino)-2-fluorophenyl)-N,N-dimethylbutanamide (75) (12 mg, 89%): $^1$H NMR δ 7.04 (dd, 1H, J=8.0, 7.8 Hz), 6.36 (dd, 1H, J=8.0, 2.3 Hz), 6.32 (dd, 1H, J=11.6, 2.3 Hz), 4.08 (br s, 1H), 2.96 (s, 3H), 2.93 (s, 3H), 2.77-2.81 (m, 2H), 2.61 (t, 2H, J=7.4 Hz), 2.35-2.38 (m, 2H), 2.31 (t, 2H, J=7.6 Hz), 2.10-2.37 (m, 2H), 1.87-1.95 (m, 2H).

4-(4-(7-(4-Cyano-3-(trifluoromethyl)phenyl)-8-oxo-6-thioxo-5,7-diazaspiro[3.4]oct-an-5-yl)-2-fluorophenyl)-N,N-dimethylbutanamide (74) [ND-8]

A mixture of 4-(4-(2-Cyanopropan-2-ylamino)-2-fluorophenyl)-N,N-dimethylbutanamide (75) (7 mg, 0.02 mmol) and 4-isothiocyanato-2-trifluoromethylbenzonitrile (96) (12 mg, 0.05 mmol) in DMF (1 mL) was heated to 80° C. using microwave for 16 h. To this mixture was added methanol (3 mL) and aq. 1 N HCl (3 mL). The second mixture was refluxed for 1.5 h. After being cooled to room temperature, the reaction mixture was poured into cold water (30 mL) and extracted with ethyl acetate (30 mL). The organic layer was dried over MgSO$_4$, concentrated and the residue was purified with silica gel column chromatography (dichloromethane:acetone, 95:5) to give 4-(4-(7-(4-Cyano-3-(trifluoromethyl)phenyl)-8-oxo-6-thioxo-5,7-diazaspiro[3.4]oct-an-5-yl)-2-fluorophenyl)-N,N-dimethylbutanamide (74) [ND-8](8 mg, 65%) as a pale yellowish solid: $^1$H NMR δ 7.98 (d, 1H, J=8.2 Hz), 7.97 (d, 1H, J=2.1 Hz), 7.84 (dd, 1H, J=8.2, 2.1 Hz), 7.46 (dd, 1H, J=8.0, 8.0 Hz), 7.05 (dd, 1H, J=8.0, 2.2 Hz), 7.02 (dd, 1H, J=9.6, 2.2 Hz), 3.01 (s, 3H), 2.97 (s, 3H), 2.80 (t, 2H, J=7.8 Hz), 2.63-2.71 (m, 2H), 2.52-2.62 (m, 2H), 2.42 (t, 2H, J=7.4 Hz), 2.20-2.31 (m, 1H), 2.00-2.08 (m, 2H), 1.65-1.75 (m, 1H); $^{13}$C NMR δ 179.9, 174.7 (2 C's), 161.3 (d, J=248 Hz), 137.0, 135.2, 134.1 (d, J=10.3 Hz), 133.6 (q, J=33.3 Hz), 132.1, 131.9 (d, J=5.7 Hz), 131.2 (d, J=16.2 Hz), 127.1, 125.7 (d, J=4.3 Hz), 121.9 (q, J=272 Hz), 117.2 (d, J=25.1 Hz), 114.8, 110.2, 67.5, 37.2, 35.5, 32.7, 31.6, 28.5, 25.2, 13.7.

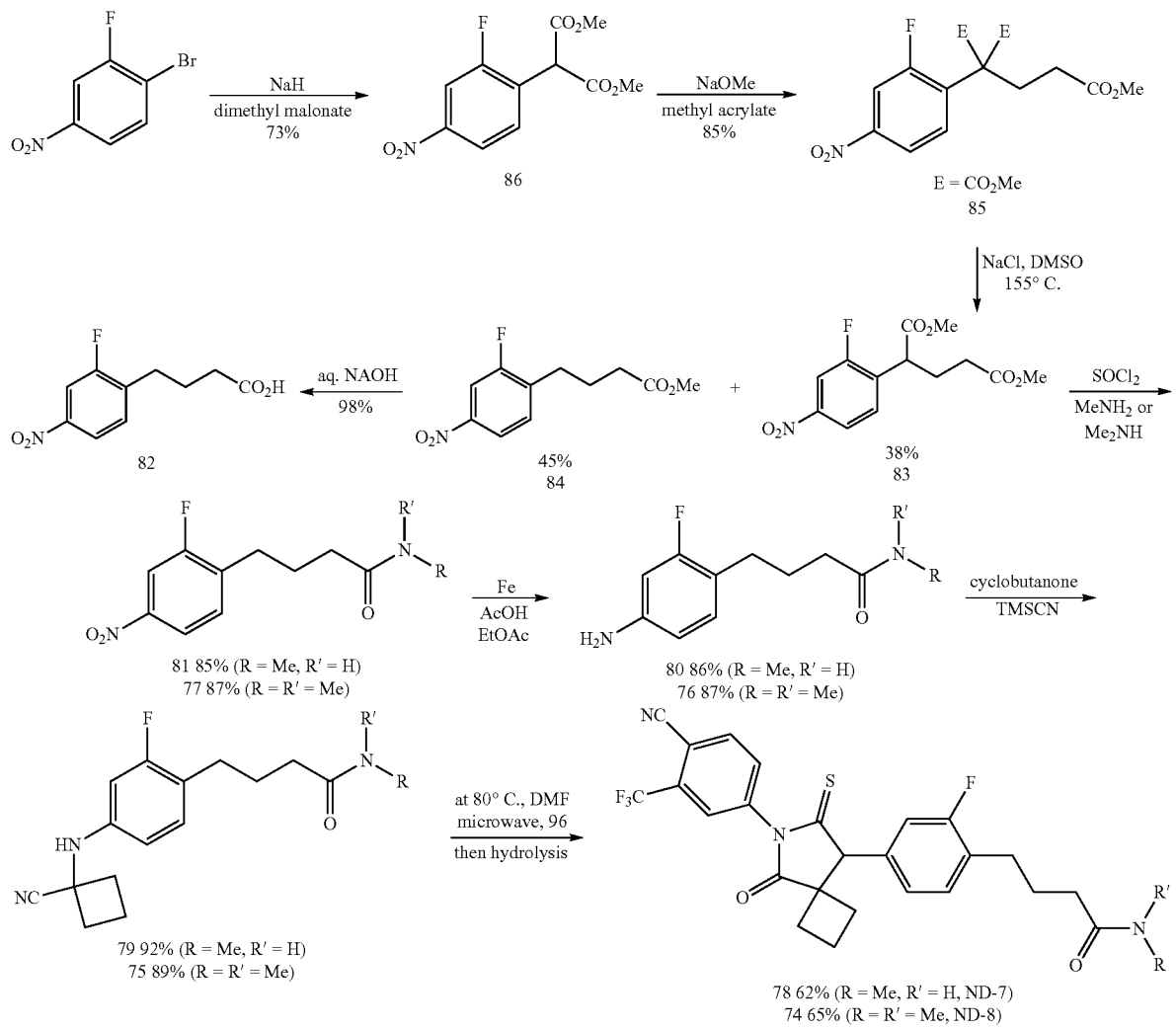

Synthesis of ND-9

Dimethyl 2-(2-cyanoethyl)-2-(2-fluoro-4-nitrophenyl)malonate (73)

To a solution of the nitro diester, Dimethyl 2-(2-fluoro-4-nitrophenyl)malonate (86) (0.4 g, 1.47 mmol) and acrylonitrile (0.11 mL, 1.62 mmol) in absolute methanol (5 mL) was added a catalytic amount of sodium methoxide at 21° C. under argon. The reaction mixture was stirred for 40 h at the same temperature and then diluted with dichloromethane (50 mL). The resulting mixture was washed with water, brine and dried. The residue obtained upon evaporation of the solvents was purified on a silica gel (hexane:ethyl acetate, 8:1) to give Dimethyl 2-(2-cyanoethyl)-2-(2-fluoro-4-nitrophenyl)malonate (73) (0.25 g, 52%): $^1$H NMR δ 8.07 (dd, 1H, J=8.7, 2.3 Hz), 7.99 (dd, 1H, J=10.9, 2.3 Hz), 7.47 (dd, 1H, J=8.7, 7.3 Hz), 3.85 (s, 6H), 2.65-2.70 (m, 2H), 2.47-2.51 (m, 2H).

4-(2-Fluoro-4-nitrophenyl)butanenitrile (72)

A solution of compound Dimethyl 2-(2-cyanoethyl)-2-(2-fluoro-4-nitrophenyl)malonate (73) (0.19 g, 0.59 mmol), sodium chloride (0.10 g, 1.76 mmol) and water (0.15 mL) in distilled dimethylsulfoxide (DMSO, 4 mL) was heated to 155° C. overnight. The reaction mixture was allowed to cool to 21° C. and then worked up by adding water and extracting with ethyl acetate (2×50 mL). The organic layer was dried over MgSO$_4$, concentrated and the residue was purified with silica gel column chromatography (hexane:ethyl acetate, 8:1) to give desired 4-(2-Fluoro-4-nitrophenyl)butanenitrile (72) (79 mg, 65%): $^1$H NMR δ 8.02 (dd, 1H, J=8.3, 2.2 Hz), 7.94 (dd, 1H, J=9.5, 2.2 Hz), 7.42 (dd, 1H, J=8.3, 7.4 Hz), 2.93 (t, 2H, J=7.7 Hz), 2.41 (t, 2H, J=7.0 Hz), 2.01-2.07 (m, 2H).

4-(4-Amino-2-fluorophenyl)butanenitrile (71)

A solution of compound 4-(2-Fluoro-4-nitrophenyl)butanenitrile (72) (47 mg, 0.23 mmol), Fe (78 mg, 1.40 mmol) and acetic acid (1 mL) in ethyl acetate (3 mL) was heated under reflux for 2 h. The reaction mixture was allowed to cool to 21° C. and then filtered. The organic layer was concentrated and the residue was purified with silica gel column chromatography (dichloromethane:acetone, 9:1) to give desired 4-(4-Amino-2-fluorophenyl)butanenitrile (71)

(33 mg, 83%): ¹H NMR δ 6.98-7.01 (m, 1H), 6.46-6.52 (m, 2H), 2.70 (t, 2H, J=7.6 Hz), 2.32 (t, 2H, J=7.2 Hz), 1.89-1.98 (m, 2H).

1-(4-(3-Cyanopropyl)-3-fluorobenzyl)cyclobutanecarbonitrile (70)

A mixture of 4-(4-Amino-2-fluorophenyl)butanenitrile (71) (30 mg, 0.17 mmol), cyclobutanone (24 mg, 0.34 mmol) and trimethylsilyl cyanide (TMSCN, 33 mg, 0.34 mmol) was heated to 80° C. and stirred for 15 h. To the medium was added ethyl acetate (2×20 mL) and then washed with water (2×20 mL). The organic layer was dried over MgSO₄ and concentrated and the residue was purified with silica gel column chromatography (dichloromethane: acetone, 9:1) to give 1-(4-(3-Cyanopropyl)-3-fluorobenzyl)cyclobutanecarbonitrile (70) (40 mg, 92%): ¹H NMR δ 7.01 (dd, 1H, J=8.0, 7.5 Hz), 6.37 (dd, 1H, J=8.0, 2.4 Hz), 6.34 (dd, 1H, J=11.8, 2.4 Hz), 4.18 (br s, 1H), 2.76-2.81 (m, 2H), 2.70 (t, 2H, J=7.3 Hz), 2.33-2.39 (m, 2H), 2.33 (t, 2H, J=7.1 Hz), 2.12-2.30 (m, 2H), 1.90-1.95 (m, 2H).

for 1.5 h. After being cooled to room temperature, the reaction mixture was poured into cold water (30 mL) and extracted with ethyl acetate (30 mL). The organic layer was dried over MgSO₄, concentrated and the residue was purified with silica gel column chromatography (dichloromethane:acetone, 95:5) to give 4-(5-(4-(3-Cyanopropyl)-3-fluorophenyl)-8-oxo-6-thioxo-5,7-diazaspiro[3.4]octan-7-yl)-2-(trifluoromethyl)benzonitrile (69) [ND-9](48 mg, 80%) as a pale yellowish solid: ¹H NMR δ 7.98 (d, 1H, J=8.2 Hz), 7.97 (d, 1H, J=2.0 Hz), 7.84 (dd, 1H, J=8.2, 2.0 Hz), 7.44 (dd, 1H, J=8.0, 8.0 Hz), 7.10 (dd, 1H, J=8.0, 2.0 Hz), 7.07 (dd, 1H, J=10.2, 2.0 Hz), 2.92 (t, 2H, J=7.6 Hz), 2.64-2.71 (m, 2H), 2.51-2.61 (m, 2H), 2.45 (t, 2H, J=7.1 Hz), 2.20-2.31 (m, 1H), 2.03-2.11 (m, 2H), 1.64-1.75 (m, 1H); ¹³C NMR δ 179.9, 174.6, 161.3 (d, J=248 Hz), 137.0, 135.2, 134.9 (d, J=10.0 Hz), 133.6 (q, J=33.2 Hz), 132.2, 131.9 (d, J=5.8 Hz), 129.0 (d, J=15.7 Hz), 127.1, 126.0 (d, J=3.6 Hz), 121.9 (q, J=273 Hz), 119.1, 117.6 (d, J=23.4 Hz), 114.8, 110.1, 67.4, 31.6 (2 C's), 28.1, 25.4, 16.8, 13.7.

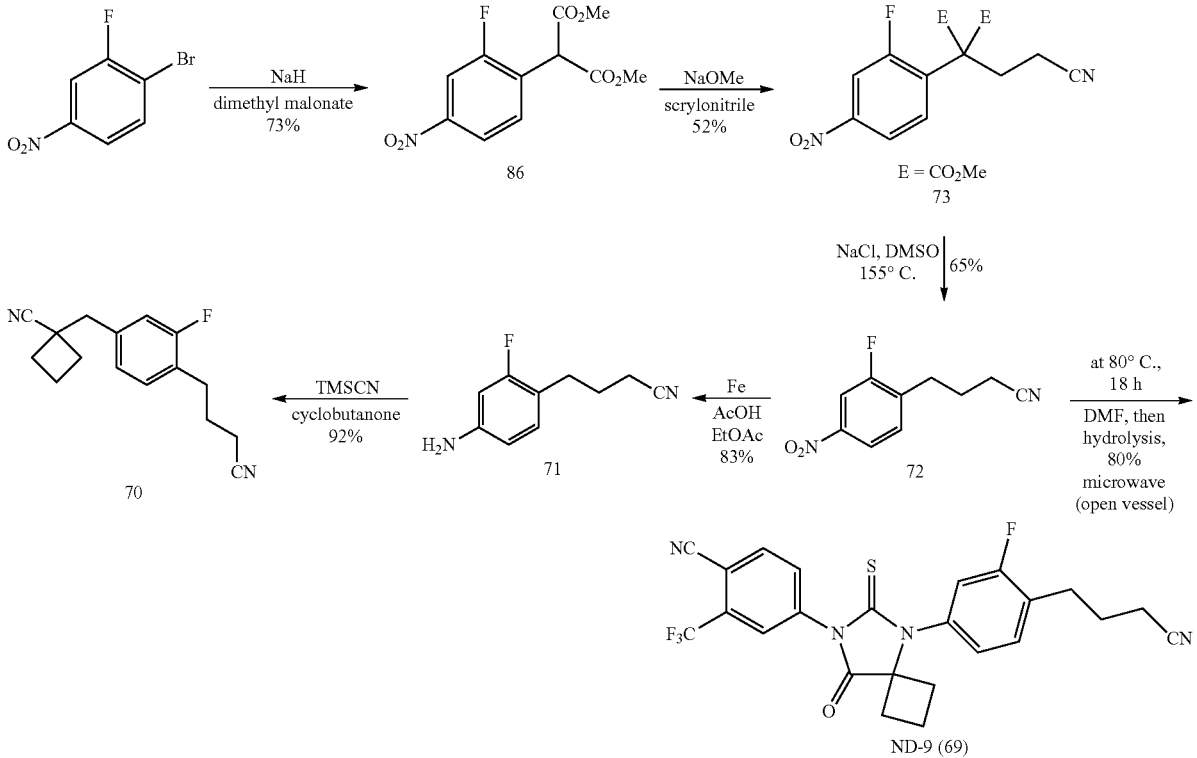

4-(5-(4-(3-Cyanopropyl)-3-fluorophenyl)-8-oxo-6-thioxo-5,7-diazaspiro[3.4]octan-7-yl)-2-(trifluoromethyl)benzonitrile (69) [ND-9]

A mixture of 1-(4-(3-Cyanopropyl)-3-fluorobenzyl)cyclobutanecarbonitrile (70) (32 mg, 0.12 mmol) and 4-isothiocyanato-2-trifluoromethylbenzonitrile (96) (62 mg, 0.27 mmol) in DMF (1 mL) was heated to 80° C. using microwave for 16 h. To this mixture was added methanol (3 mL) and aq. 1 N HCl (3 mL). The second mixture was refluxed

Synthesis of ND-11 and ND-10

4-(8-Oxo-5-(4-(4-oxobutyl)phenyl)-6-thioxo-5,7-diazaspiro[3.4]octan-7-yl)-2-(trifluoromethyl)benzonitrile (68) [ND-10]

To a stirred solution of 4-{4-[7-(4-cyano-3-trifluoromethylphenyl)-8-oxo-6-thioxo-5,7-diazaspiro[3.4]oct-5-yl]-phenyl}-butyric acid methyl ester (67) [ND-4](61 mg, 0.12 mmol) in dichloromethane (5 mL), 1M diisobutylaluminum hydride (DIBAL) solution in hexane (0.16 mL, 0.16 mmol) was added at −78° C. After 30 min, the reaction mixture was quenched with saturated Rochelle's salt solution. The resulting mixture was stirred at 21° C. until both phases were clearly separated and the organic layer was clear. After extraction, the separated organic layer was dried over MgSO$_4$, filtered, and concentrated under vacuum. The crude mixture of (66) and (68) was purified by flash column chromatography (hexane:ethyl acetate, 4:1) to give 4-(8-hydroxy-5-(4-(4-oxobutyl)phenyl)-6-thioxo-5,7-diazaspiro[3.4]octan-7-yl)-2-(trifluoromethyl) (66) (20 mg, 35%) and 4-(8-Oxo-5-(4-(4-oxobutyl)phenyl)-6-thioxo-5,7-diazaspiro[3.4]octan-7-yl)-2-(trifluoromethyl)benzonitrile (68) [ND-10](23 mg, 40%): $^1$H NMR of (68) δ 9.81 (s, 1H), 7.98 (d, NaHCO$_3$ solution. The mixture was extracted with dichloromethane. The organic layer was dried over MgSO$_4$, and evaporated in vacuo. The residue was purified by flash column chromatography (ethanol:ethyl acetate, 1:4) to give 4-(5-(4-(3-(4,5-Dihydro-1H-imidazol-2-yl)propyl)phenyl)-8-oxo-6-thioxo-5,7-diaza-spiro[3.4]octan-7-yl)-2-(trifluoromethyl)benzonitrile (65) [ND-11](6 mg, 35%): $^1$H NMR δ 7.98 (d, 1H, J=1.9 Hz), 7.97 (d, 1H, J=8.3 Hz), 7.85 (dd, 1H, J=8.3, 1.9 Hz), 7.46 (d, 1H, J=8.2 Hz), 7.25 (d, 1H, J=8.2 Hz), 4.72 (br s, 1H), 3.67-3.80 (m, 4H), 2.85-3.05 (m, 2H), 2.57-2.70 (m, 2H), 2.43-2.57 (m, 4H), 2.15-2.30 (m, 1H), 1.63-1.80 (m, 3H).

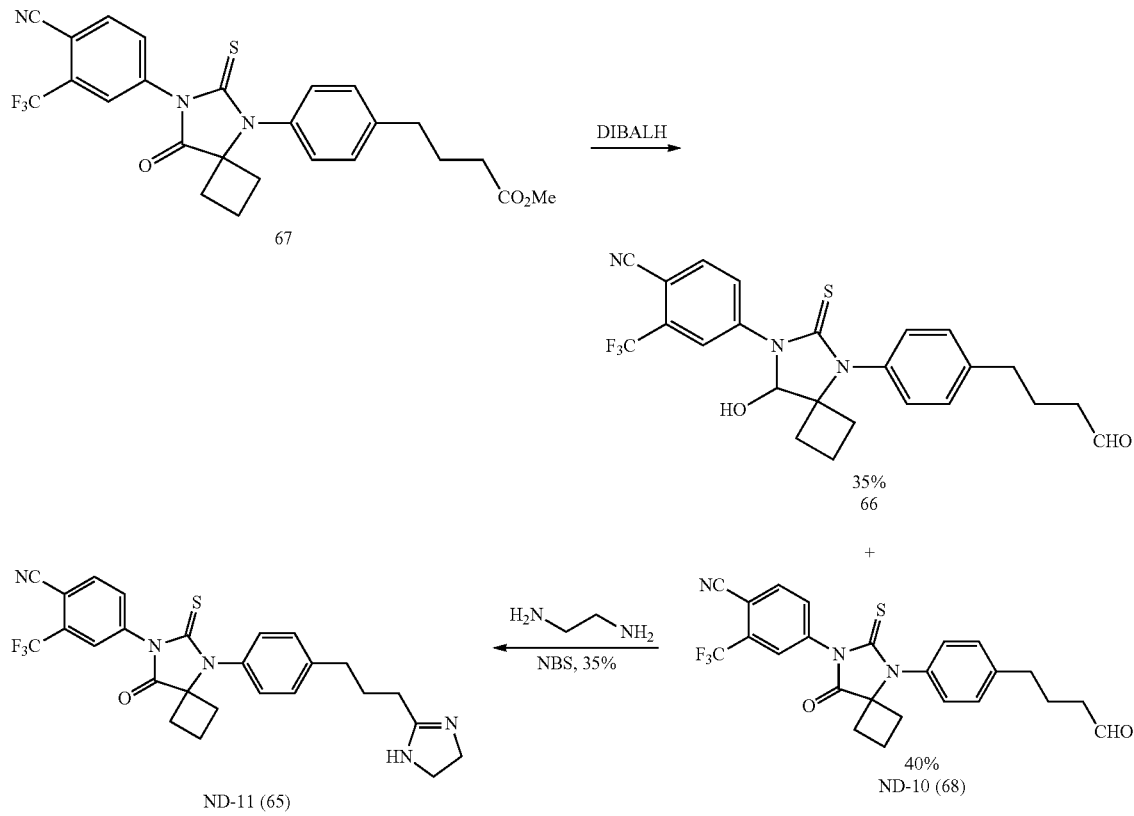

1H, J=2.0 Hz), 7.97 (d, 1H, J=8.0 Hz), 7.86 (dd, 1H, J=8.2, 2.0 Hz), 7.40 (d, 1H, J=8.3 Hz), 7.24 (d, 1H, J=8.3 Hz), 2.76 (t, 2H, J=7.5 Hz), 2.63-2.67 (m, 2H), 2.57-2.63 (m, 2H), 2.55 (t, 2H, J=7.2 Hz), 2.13-2.31 (m, 1H), 2.01-2.07 (m, 2H), 1.57-1.77 (m, 1H).

4-(5-(4-(3-(4,5-Dihydro-1H-imidazol-2-yl)propyl)phenyl)-8-oxo-6-thioxo-5,7-diaza-spiro[3.4]octan-7-yl)-2-(trifluoromethyl)benzonitrile (65) [ND-11]

The mixture of 4-(8-Oxo-5-(4-(4-oxobutyl)phenyl)-6-thioxo-5,7-diazaspiro[3.4]octan-7-yl)-2-(trifluoromethyl)benzonitrile (68) [ND-10](15 mg, 0.03 mmol) and ethylene diamine (2 µL, 0.04 mmol) in dry dichloromethane (3 mL) was stirred at 0° C. for 30 min under argon. N-Bromosuccinimide (NBS, 6 mg, 0.04 mmol) was added to the mixture and the resulting solution was stirred overnight at 21° C. Reaction was quenched by the addition of saturated Synthesis of ND-12

4-(4-Nitrophenyl)butanal (64)

To a stirred solution of methyl 4-(4-nitrophenyl)butanoate (63) (0.45 g, 2.02 mmol) in dichloromethane (30 mL), 1M diisobutylaluminum hydride (DIBAL) solution in hexane (2.62 mL, 2.62 mmol) was added at −78° C. After 30 min, the reaction mixture was quenched with saturated Rochelle's salt solution. The resulting mixture was stirred at 21° C. until both phases were clearly separated and the organic layer was clear. After extraction, the separated organic layer was dried over MgSO$_4$, filtered, and concentrated under vacuum. The crude 4-(4-Nitrophenyl)butanal (64) was purified by flash column chromatography (hexane:ethyl acetate, 8:1) to give 4-(4-Nitrophenyl)butanal (64) (0.28 g, 72%): $^1$H NMR δ

9.79 (s, 1H), 8.16 (d, 2H, J=8.7 Hz), 7.34 (d, 2H, J=8.7 Hz), 2.77 (t, 2H, J=7.7 Hz), 2.51 (t, 2H, J=7.1 Hz), 1.95-2.04 (m, 2H).

2-(3-(4-Nitrophenyl)propyl)-4,5-dihydro-1H-imidazole (62)

The mixture of 4-(4-Nitrophenyl)butanal (64) (0.28 g, 1.45 mmol) and ethylene diamine (0.1 mL, 1.59 mmol) in dry dichloromethane (10 mL) was stirred at 0° C. for 30 min under argon. NBS (0.26 g, 1.59 mmol) was added to the mixture and the resulting solution was stirred overnight at 21° C. Reaction was quenched by the addition of saturated NaHCO$_3$ solution. The mixture was extracted with dichloromethane. The organic layer was dried over MgSO$_4$, and evaporated in vacuo. The residue was purified by flash column chromatography (ethanol:ethyl acetate:triethylamine, 1:1:0.2) to give 2-(3-(4-Nitrophenyl)propyl)-4,5-dihydro-1H-imidazole (62) (0.26 g, 76%): $^1$H NMR δ 8.14 (d, 2H, J=8.7 Hz), 7.35 (d, 2H, J=8.7 Hz), 3.59 (s, 4H), 2.79 (t, 2H, J=7.7 Hz), 2.26 (t, 2H, J=7.4 Hz), 1.96-2.05 (m, 2H).

An alternative route for synthesizing 2-(3-(4-Nitrophenyl)propyl)-4,5-dihydro-1H-imidazole (62) from methyl 4-(4-nitrophenyl)butanoate (63) was also used and is as follows. Ethylenediamine (0.1 mL, 1.59 mmol) was added dropwise to a stirred solution of trimethylaluminum (1.59 mmol) in 2 mL of toluene, so that the temperature did not exceed 10° C. At the end of methane evolution the ester (63) (0.22 g, 1.00 mmol) was gradually added at room temperature. The reaction mixture was refluxed for 3 h. After cooling, the solution was treated dropwise with 1 mL of water, diluted with 3 mL of methanol and 3 mL of methylene chloride, and refluxed on a steam bath for 15 min. After filtration over MgSO$_4$ and solvent evaporation the residue was purified by flash column chromatography (ethanol:ethyl acetate:triethylamine, 1:1:0.2) to give 2-(3-(4-Nitrophenyl)propyl)-4,5-dihydro-1H-imidazole (62) (0.10 g, 45%): $^1$H NMR δ 8.14 (d, 2H, J=8.7 Hz), 7.35 (d, 2H, J=8.7 Hz), 3.59 (s, 4H), 2.79 (t, 2H, J=7.7 Hz), 2.26 (t, 2H, J=7.4 Hz), 1.96-2.05 (m, 2H).

tert-Butyl 2-(3-(4-nitrophenyl)propyl)-1H-imidazole-1-carboxylate (61)

To a solution of dichloromethane (5 mL) and dimethylsulfoxide (0.06 mL, 0.79 mmol) was added oxalyl chloride (0.07 mL, 0.79 mmol) at −78° C. under an argon atmosphere. After stirring for 20 min, a solution of 2-(3-(4-Nitrophenyl)propyl)-4,5-dihydro-1H-imidazole (62) (74 mg, 0.32 mmol) in dichloromethane was added to the reaction mixture. After stirring for 50 min, triethylamine (0.22 mL, 1.59 mmol) was added and then the reaction mixture was warmed to room temperature. After stirring for 50 min, aqueous ammonia solution (10 mL) was added and the resulting mixture was extracted with chloroform (20 mL). The combined organic layer was washed with brine, dried, filtered and concentrated under reduced pressure. The residue was purified by flash column chromatography (dichloromethane:methanol, 10:1) to give the corresponding imidazole (61 mg, 83%). To a solution of the imidazole (50 mg, 0.22 mmol) in dichloromethane (5 mL) was added triethylamine (0.04 mL, 0.26 mmol) and tert-butoxycarbonyl anhydride (Boc$_2$O, 57 mg, 0.26 mmol). The reaction mixture was stirred at 21° C. overnight. The reaction mixture was extracted with dichloromethane (20 mL). The organic layer was washed with brine, dried, filtered and concentrated under reduced pressure. The residue was purified by flash column chromatography (dichloromethane:methanol, 20:1) to give tert-Butyl 2-(3-(4-nitrophenyl)propyl)-1H-imidazole-1-carboxylate (61) (72 mg, quant.): $^1$H NMR δ 8.14 (d, 2H, J=8.7 Hz), 7.37 (d, 2H, J=8.7 Hz), 7.30 (d, 1H, J=1.7 Hz), 6.86 (d, 1H, J=1.7 Hz), 3.05 (t, 2H, J=7.6 Hz), 2.85 (t, 2H, J=7.7 Hz), 2.11-2.19 (m, 2H), 1.60 (s, 9H).

tert-Butyl 2-(3-(4-(1-cyanocyclobutylamino)phenyl)propyl)-1H-imidazole-1-carboxylate (60)

To a solution of tert-Butyl 2-(3-(4-nitrophenyl)propyl)-1H-imidazole-1-carboxylate (61) (72 mg, 0.22 mmol) in ethyl acetate (5 mL) was introduced hydrogen gas in the presence of a catalytic amount of Pd/C. After completion of the reaction, the reaction mixture was filtered, concentrated and then purified by flash column chromatography (dichloromethane:methanol, 10:1) to give the corresponding amine (59 mg, 90%): $^1$H NMR δ 7.30 (d, 1H, J=1.7 Hz), 7.00 (d, 2H, J=8.3 Hz), 6.85 (d, 1H, J=1.7 Hz), 6.62 (d, 2H, J=8.3 Hz), 3.54 (br s, 2H), 3.01 (t, 2H, J=7.8 Hz), 2.62 (t, 2H, J=7.7 Hz), 2.01-2.08 (m, 2H), 1.65 (s, 9H). A mixture of the amine (55 mg, 0.18 mmol), cyclobutanone (26 mg, 0.36 mmol) and trimethylsilyl cyanide (TMSCN, 36 mg, 0.36 mmol) was heated to 80° C. and stirred for 15 h. To the medium was added ethyl acetate (2×20 mL) and then washed with water (2×20 mL). The organic layer was dried over MgSO$_4$ and concentrated and the residue was purified with silica gel column chromatography (dichloromethane:acetone, 9:1) to give tert-Butyl 2-(3-(4-(1-cyanocyclobutylamino)phenyl)propyl)-1H-imidazole-1-carboxylate (60) (57 mg, 82%): 1H NMR δ 7.30 (d, 1H, J=1.7 Hz), 7.09 (d, 2H, J=8.4 Hz), 6.85 (d, 1H, J=1.7 Hz), 6.58 (d, 2H, J=8.4 Hz), 3.92 (br s, 1H), 3.01 (t, 2H, J=7.7 Hz), 2.74-2.80 (m, 2H), 2.64 (t, 2H, J=7.6 Hz), 2.29-2.42 (m, 2H), 2.10-2.27 (m, 2H), 2.01-2.09 (m, 2H), 1.60 (s, 9H).

4-(5-(4-(3-(1H-Imidazol-2-yl)propyl)phenyl)-8-oxo-6-thioxo-5,7-diazaspiro[3.4]octan-7-yl)-2-(trifluoromethyl)benzonitrile (59) [ND-12]

A mixture of tert-Butyl 2-(3-(4-(1-cyanocyclobutylamino)phenyl)propyl)-1H-imidazole-1-carboxylate (60) (22 mg, 0.06 mmol) and 4-isothiocyanato-2-trifluoromethylbenzonitrile (96) (26 mg, 0.12 mmol) in DMF (1 mL) was heated to 80° C. using microwave for 16 h. To this mixture was added methanol (3 mL) and aq. 1 N HCl (3 mL). The 15 second mixture was refluxed for 1.5 h. After being cooled to room temperature, the reaction mixture was poured into cold water (30 mL), treated with saturated NaHCO$_3$ solution and extracted with ethyl acetate (50 mL). The organic layer was dried over MgSO$_4$, concentrated and the residue was purified with silica gel column chromatography (dichloromethane:acetone, 9:1) to give 4-(5-(4-(3-(1H-Imidazol-2-yl)propyl)phenyl)-8-oxo-6-thioxo-5,7-diazaspiro[3.4]octan-7-yl)-2-(trifluoromethyl)benzonitrile (59) [ND-12](29 mg, 52%) as a pale yellowish solid: $^1$H NMR δ 8.65 (br s, 1H), 7.97 (d, 1H, J=2.0 Hz), 7.96 (d, 1H, J=8.4 Hz), 7.84 (dd, 1H, J=8.4, 2.0 Hz), 7.34 (d, 2H, J=8.2 Hz), 7.19 (d, 2H, J=8.2 Hz), 3.00 (t, 2H, J=7.5 Hz), 2.73 (t, 2H, J=7.7 Hz), 2.47-2.77 (m, 4H), 2.13-2.25 (m, 3H), 1.51-1.71 (m, 1H).

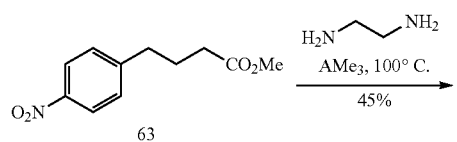
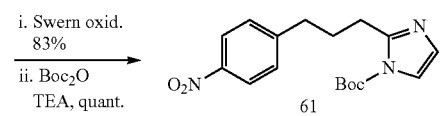
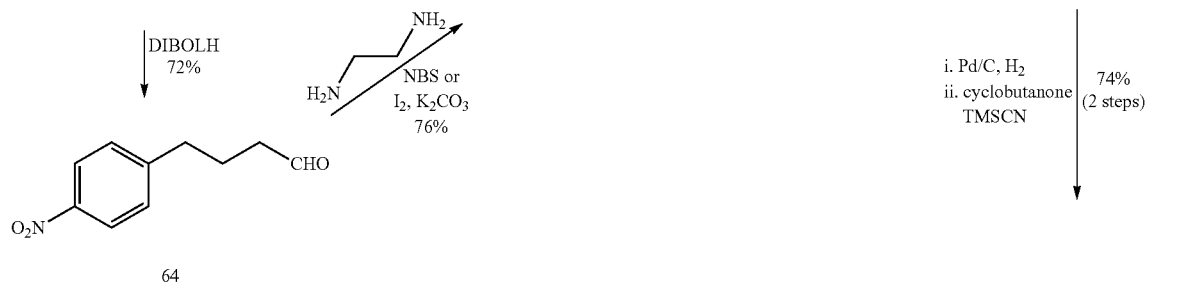
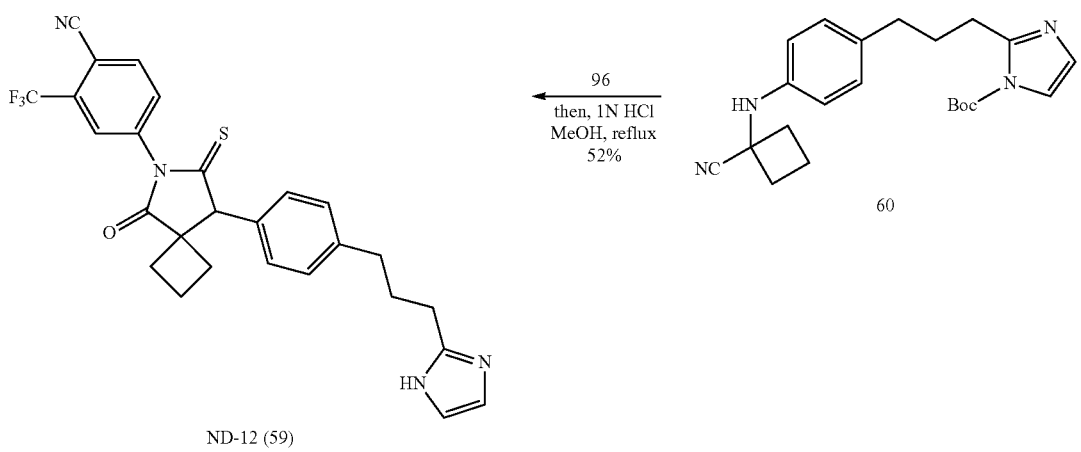

One skilled in the art could modify and/or combine the syntheses described herein to make other diarylhydantoin compounds.

Synthesis of ND-13

4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113)

Another compound envisioned is 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13].

An example of a synthetic route for making 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13] is below.

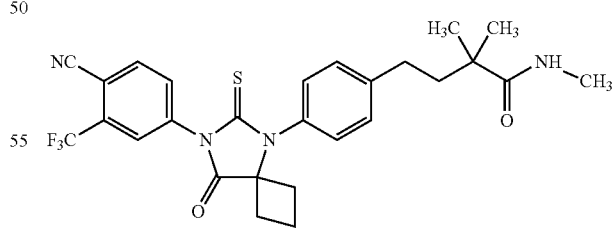

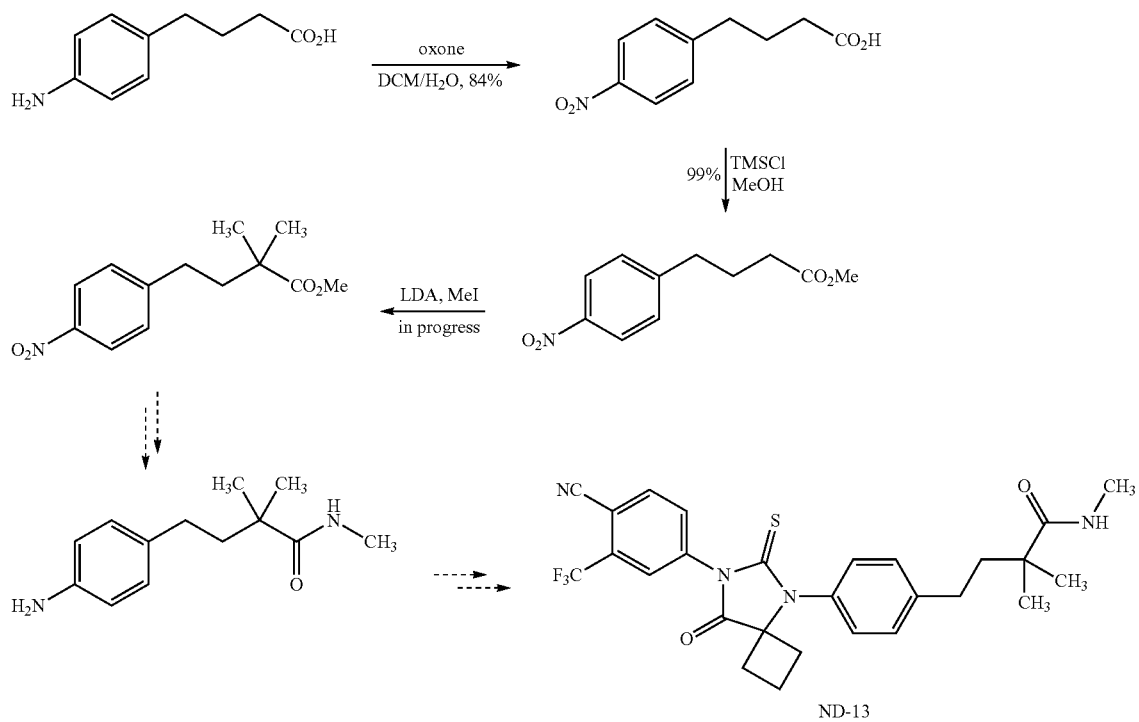

Alternatively, 4-(4-(7-(4-Cyano-3-(trifluoromethyl)phenyl)-8-oxo-6-thioxo-5,7-diazaspiro[3.4]oct-an-5-yl)-2-fluorophenyl)-2,2-dimethyl-N-methylbutanamide (113) [ND-13] can be synthesized in a manner similar as to that for synthesizing (92) [ND-2]. A mixture of 4-Isothiocyanato-2-trifluoromethylbenzonitrile (96) and 4-(4-(1-cyanocyclobutylamino)phenyl)-N,2,2-trimethylbutanamide (111) in solvent, for example, in DMF, is heated under microwave irradiation at 80° C. for 6 h.

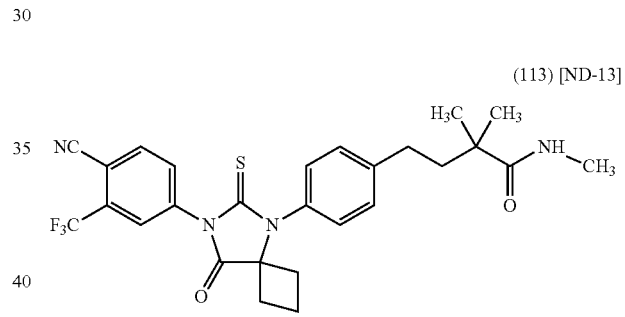

To this mixture is added alcohol, e.g., methanol, and acid, e.g., aqueous hydrochloric acid. The second mixture is refluxed for 1.5 h. After being cooled to room temperature, the reaction mixture is poured into cold water and extracted, for example, with ethyl acetate. The organic layer is dried, e.g., dried over $MgSO_4$, concentrated, and the residue is purified, for example, by silica gel column chromatography using hexane:ethyl acetate (2:1), to give 4-(4-(7-(4-Cyano-3-(trifluoromethyl)phenyl)-8-oxo-6-thioxo-5,7-diazaspiro [3.4]oct-an-5-yl)-2-fluorophenyl)-2,2-dimethyl-N-methylbutanamide (113) [ND-13].

Inventive compounds also include those with the following formulas.

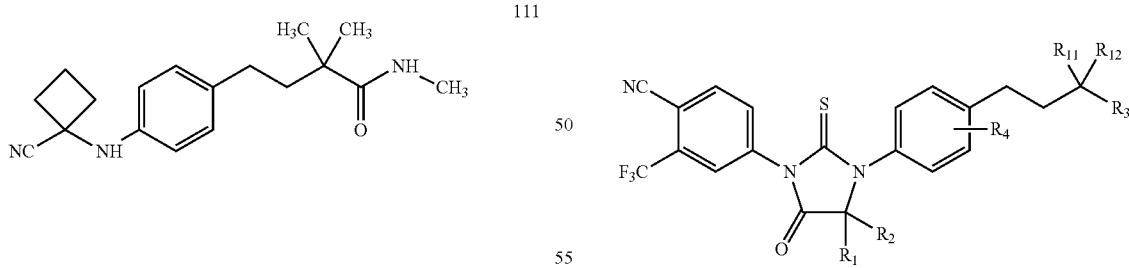

$R_1$ and $R_2$ together can comprise eight or fewer carbon atoms and can be alkyl, substituted alkyl, or, together with the carbon to which they are linked, a cycloalkyl or substituted cycloalkyl group. $R_3$ can be hydrogen, cyano, formyl,

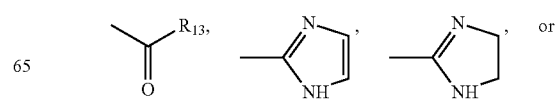

-continued

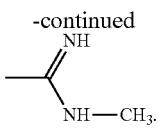

$R_4$ can be hydrogen, F, Cl, Br, and I. $R_{11}$ and $R_{12}$ can be the same or different and can be hydrogen or methyl. $R_{13}$ can be hydrogen or —$NR_{14}R_{15}$. $R_{14}$ and $R_{15}$ can be the same or different and can be hydrogen or methyl.

Pharmacological Examination of the Compounds

Compounds for which synthetic routes are described above can be evaluated through screening on hormone refractory prostate cancer cells for antagonistic and agonistic activities against AR utilizing screening procedures similar to those in PCT applications bearing numbers US04/42221, US05/05529, and US06/11417 and U.S. application Ser. No. 11/433,829, which are hereby incorporated by reference.

In Vitro Biological Assay

Effect of Compounds on AR by a Reporter Assay

For example, the compounds can be subjected to tests using an artificial androgen receptor (AR) response reporter system in a hormone refractory prostate cancer cell line. The prostate cancer LNCaP cells are engineered to stably express about 5-fold higher level of AR than endogenous level. The exogenous AR has similar properties to endogenous AR in that both are stabilized by a synthetic androgen R1881. The AR-over expressed cells are also engineered to stably incorporate an AR response reporter and the reporter activity of these cells shows features of hormone refractory prostate cancer. It responds to low concentration of a synthetic androgen R1881, is inhibited only by high concentrations of bicalutamide, and displays agonistic activity with bicalutamide. Bicalutamide inhibits AR response reporter and does not have agonistic activity in hormone sensitive prostate cancer cells.

The antagonistic activity of the compounds for which the synthesis is described above can be examined in the presence of 100 pM of R1881. Engineered LNCaP cells (LNCaP-AR, also abbreviated LN-AR) are maintained in Iscove's medium containing 10% fetal bovine serum (FBS). Two days prior to drug treatment, the cells are grown in Iscove's medium containing 10% charcoal-stripped FBS (CS-FBS) to deprive of androgens. The cells are split and grown in Iscove's medium containing 10% CS-FBS with 100 pM of R1881 and increasing concentrations of test compounds. After two days of incubation, reporter activities are assayed. Bicalutamide is used as a control substance.

One previously unrecognized property of AR overexpression in hormone refractory prostate cancer is its ability to switch antagonists to agonists. Therefore, only those compounds with minimal or no agonistic activities are qualified to be anti-androgens for this disease. To determine agonistic activities of different compounds, the stimulating activities on androgen receptor (AR) using the AR response reporter as the measure in the LN-AR system in the absence of R1881 can be examined. Bicalutamide can activate AR in hormone refractory prostate cancer. RU59063 and other anti-androgenic compounds listed as examples in U.S. Pat. No. 5,705,654 can activate AR in hormone refractory prostate cancer.

To examine the specificity of AR inhibitors, compounds can be tested in LNCaP cells with an over expression of glucocorticoid receptor (GR), the closest member of AR in the nuclear receptor family. These cells also carry a GR response reporter and the reporter activity can be induced by dexamethasone, a GR agonist, and the induction can be blocked by RU486, a GR inhibitor.

Effect of Compounds on AR by Measuring Secreted Levels of Prostate Specific Antigen (PSA)

PSA levels are indicators of androgen receptor (AR) activities in prostate cancer. To examine if the compounds affect AR function in a physiological environment, secreted levels of endogenous PSA induced by R1881 in the AR-overexpressed LNCaP cells (LNCaP-AR, also abbreviated LN-AR) can be determined. The LNCaP-AR cells are a line of lymph node carcinoma of prostate cells transduced with a plasmid that makes express androgen receptors. LNCaP-AR cells are maintained in Iscove's medium containing 10% FBS. Two days prior to drug treatment, the cells are grown in Iscove's medium containing 10% CS-FBS to deprive of androgens. The cells are split and grown in Iscove's medium containing 10% CS-FBS with appropriate concentrations of R1881 and the test compounds. After four days incubation, secreted PSA levels are assayed using PSA ELISA kits (American Qualex, San Clemente, Calif.)

The secreted PSA level of LNCaP-AR cells are strongly induced by 25 pM of R1881. In contrast, PSA is not induced in the parental LNCaP cells until concentration of R1881 reached 100 pM. Thus, the AR in hormone refractory prostate cancer is hyper-sensitive to androgens. A dose-dependent inhibition on AR activity is carried out to determine the IC50s of different compounds in inhibiting PSA expression.

Agonistic activities of selective compounds on AR in hormone refractory prostate cancer can be examined using secreted PSA as the surrogate marker. To do this, androgen-starved AR over expressed LNCaP cells are incubated with increasing concentrations of the compounds for which a synthesis is described above in the absence of R1881 and secreted PSA in the culture medium are measured 4 days later.

RU59063 and other antiandrogenic compounds listed as examples in U.S. Pat. No. 5,705,654 can stimulate PSA expression in hormone refractory prostate cancer.

Effect of Compounds on AR Mitochondrial Activity by MTS Assay

LNCaP-AR cells can be maintained in Iscove's medium containing 10% FBS. The compounds are examined for their effect on growth of hormone refractory prostate cancer cells. Overexpressed LNCaP cells are used because these cells behave as hormone refractory prostate cancer cells in vitro and in vivo. Mitochondria activity by MTS assay is measured, a surrogate for growth. LNCaP cells with overexpressed AR (LN-AR) are maintained in Iscove's medium containing 10% FBS. Two days prior to drug treatment, the cells are grown in Iscove's medium containing 10% CS-FBS to deprive of androgens. The cells are then split and grown in Iscove's medium containing 10% CS-FBS with appropriate concentrations of R1881 and increasing concentrations of the test compounds. After four days incubation, cell growth is monitored by MTS (Promega, Madison, Wis.).

Consistent with the reporter assay and PSA assay, growth of the AR-overexpressed LNCaP is stimulated by 25 microM of R1881, but the parental cells are not stimulated until R1881 concentration reaches 100 microM. The inhibitory effect of compounds on growth of hormone refractory prostate cancer in the presence of 100 pM of R1881 is measured. Bicalutamide does not inhibit hormone refractory prostate cancer.

To examine whether growth inhibition in the MTS assay occurs by targeting AR, compounds can be tested in DU-145 cells, a prostate cancer cell line that lacks AR expression. The compounds can be tested for their ability to inhibit cells other than AR-expressed prostate cancer cells, such as MCF7 and SkBr3, two commonly used breast cancer cells, or 3T3, a normal mouse fibroblast cell line.

Based on the observations with various assays, the compounds can be ranked in order of their activity.

Inhibitory Effect on Hormone Refractory Prostate Cancer Xenograft Tumors

The in vivo effects of compounds on hormone refractory prostate cancer can be examined. The effect of compounds on xenograft tumors established from AR-overexpressed LNCaP cells can be examined. The engineered cells in Matrigel (Collaborative Biomedical) are injected subcutaneously into the flanks of the castrated male SCID mice. Tumor size is measured weekly in three dimensions using calipers. After xenograft tumors become established (for example, with a tumor size of at least 40 mm$^3$), mice with tumors are randomized and treated with different doses of compounds orally once daily. Bicalutamide does not inhibit growth of hormone refractory prostate cancer, the same as vehicle.

Compounds can also be tested in another xenograft model of hormone refractory prostate cancer, hormone refractory LAPC4. This model is established from passaging of hormone sensitive prostate cancer in castrated mice, which mimics the clinical progression of prostate cancer. Bicalutamide does not inhibit growth and PSA expression in hormone refractory LAPC4 xenograft model, the same as vehicle.

Inhibitory Effect on Growth of Hormone Sensitive Prostate Cancer Cells

To determine if compounds inhibit hormone sensitive prostate cancer cells, the effect of the compounds on growth of LNCaP cells can be examined by measuring MTS of mitochondria activities. Bicalutamide mildly inhibits hormone sensitive LNCaP cells in a dose-dependent manner.

In Vivo Biological Assay

Animal experiments are performed in compliance with the guidelines of the Animal Research Committee of the University of California at Los Angeles. Animals are bought from Taconic and maintained in a laminar flow tower in a defined flora colony. LNCaP-AR and LNCaP-vector cells are maintained in RPMI medium supplemented with 10% FBS. $10^6$ cells in 100 µl of 1:1 Matrigel to RPMI medium are injected subcutaneously into the flanks of intact or castrated male SCID mice. Tumor size is measured weekly in three dimensions (length×width×depth) using calipers. Mice are randomized to treatment groups when tumor size reaches approximately 100 mm$^3$. Drugs are given orally every day at 10 mg/kg and 50 mg/kg. To obtain pharmacodynamic readout, the animals are imaged via an optical CCD camera, 3 hours after last dose of the treatment. An ROI is drawn over the tumor for luciferase activity measurement in photon/second.

The pharmacokinetics of bicalutamide and compounds being tested is evaluated in vivo using 8 week-old FVB mice which are purchased from Charles River Laboratories. Mice are divided into groups of three for each time points. Two mice are not treated with drug and two other mice are treated with vehicle solution. Each group is treated with 10 mg per kilogram of body weight.

The drug is dissolved in a mixture 1:5:14 of DMSO:PEG400:H$_2$O. (Vehicle solution) and is administered into mice through the tail vein. The animals are warmed under a heat lamp for approximately 20 minutes prior to treatment to dilate their tail vein. Each mouse is placed into a mouse restrainer (Fisher Sci. Cat#01-288-32A) and is injected with 200 µl of drug in vehicle solution into the dilated tail vein. After drug administration, the animals are euthanized via CO$_2$ inhalation at different timepoints: 5 mn, 30 mn, 2 h, 6 h, 16 h. Animals are immediately bled after exposure to CO$_2$ via cardiac puncture (1 ml BD syringe+27G ⅝ needle). For oral dosage, the drug is dissolved in a mixture 50:10:1:989 of DMSO:Carboxymethylcellulose:Tween80:H$_2$O before oral administration via a feeding syringe.

The serum samples are analyzed to determine the drug's concentration by the HPLC which (Waters 600 pump, Waters 600 controller and Waters 2487 detector) is equipped with an Alltima C18 column (3µ, 150 mm×4.6 mm). For example, the compounds being tested can be detected at 254 nm wave length and bicalutamide can be detected at 270 nm wave length.

The samples for HPLC analysis are prepared according to the following procedure:

Blood cells are separated from serum by centrifugation.

To 400 µl of serum are added 80 µl of a 10 µM solution of an internal standard and 520 µl of acetonitrile. Precipitation is watched for.

The mixture is vortexed for 3 minutes and then placed under ultrasound for 30 minutes.

The solid particles are filtered off or are separated by centrifugation.

The filtrate is dried under an argon flow to dryness. The sample is reconstructed to 80 µl with acetonitrile before analyzing by HPLC to determine the drug concentration. Standard curve of drug is used to improve accuracy.

The steady state concentration (Css) of a compound can be determined and compared with that of bicalutamide.

Ranking of Compounds

To rank the compounds, the following data can be considered: in vitro assays (AR response reporter system in LNCaP cell line, PSA level measurement, MTS mitochondrial assay) and in vivo experiments (tumor size measured directly or by emission induced by luciferase reporter gene, pharmacokinetic assays based on blood plasma levels). Characteristics considered in establishing a ranking can include androgen receptor (AR) antagonism activity, lack of AR agonism in hormone refractory cells, prevention of tumor growth, tumor shrinkage, and pharmacokinetic behavior, with a longer residence time in blood being advantageous.

Compounds that are highly ranked can be advantageous for use as AR antagonists, and as therapeutic agents for hormone refractory prostate cancer. They may be useful to treat other AR related diseases or conditions such as benign prostate hyperplasia, hair loss, and acne. Highly ranked compounds may also be useful as modulators of other nuclear receptors, such as glucocorticoid receptor, estrogen receptor, and peroxisome proliferator-activated receptor, and as therapeutic agents for diseases in which nuclear receptors play a role, such as breast cancer, ovarian cancer, diabetes, cardiac diseases, and metabolism related diseases. They may be useful in assays, e.g., as standards, or as intermediates or prodrugs.

The compounds presented in this application can be superior to bicalutamide in treating prostate cancer.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The diarylhydantoin compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, diarylhydantoin compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the diarylhydantoin compounds may be combined with one or more excipients and used in the form of ingestible tablets, buccal tablets, troches, capsules, elixirs, suspensions, syrups, wafers, and the like. The diarylhydantoin compounds may be combined with a fine inert powdered carrier and inhaled by the subject or insufflated. Such compositions and preparations should contain at least 0.1% diarylhydantoin compounds. The percentage of the compositions and preparations may, of course, be varied and may conveniently be between about 2% to about 60% of the weight of a given unit dosage form. The amount of diarylhydantoin compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the diarylhydantoin compounds may be incorporated into sustained-release preparations and devices. For example, the diarylhydantoin compounds may be incorporated into time release capsules, time release tablets, and time release pills.

The diarylhydantoin compounds may also be administered intravenously or intraperitoneally by infusion or injection. Solutions of the diarylhydantoin compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the diarylhydantoin compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the diarylhydantoin compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the diarylhydantoin compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the diarylhydantoin compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the diarylhydantoin compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the diarylhydantoin compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the diarylhydantoin compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 0.1 mg/kg, 1 mg/kg, 10 mg/kg, or 50 mg/kg of body weight per day.

The diarylhydantoin compounds are conveniently administered in unit dosage form; for example, containing 0.05 to 10000 mg, 0.5 to 10000 mg, 5 to 1000 mg, or about 100 mg of active ingredient per unit dosage form.

The diarylhydantoin compounds can be administered to achieve peak plasma concentrations of, for example, from about 0.5 to about 75 $\mu$M, about 1 to 50 $\mu$M, about 2 to about 30 $\mu$M, or about 5 to about 25 $\mu$M. Exemplary desirable plasma concentrations include at least or no more than 0.01, 0.025, 0.05, 0.1, 0.25, 0.5, 1, 5, 10, 25, 50, 75, 100 or 200 $\mu$M. For example, plasma levels may be from about 1 to 100 micromolar or from about 10 to about 25 micromolar. This may be achieved, for example, by the intravenous injection of a 0.05 to 5% solution of the diarylhydantoin compounds, optionally in saline, or orally administered as a bolus containing about 1-100 mg of the diarylhydantoin compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the diarylhydantoin compounds per kg of body weight.

The diarylhydantoin compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

A number of the above-identified compounds exhibit little or no agonistic activities with respect to hormone refractory prostate cancer cells. Because these compounds are strong androgen receptor (AR) inhibitors, they can be used not only in treating prostate cancer, but also in treating other AR related diseases or conditions such as benign prostate hyperplasia, hair loss, and acne. Because AR belongs to the family of nuclear receptors, these compounds may serve as scaffolds for drug synthesis targeting other nuclear receptors, such as estrogen receptor and peroxisome proliferator-activated receptor. Therefore, they may be further developed for other diseases such as breast cancer, ovarian cancer, diabetes, cardiac diseases, and metabolism related diseases, in which nuclear receptors play a role.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method for treating prostate cancer or breast cancer comprising administering a compound to a subject in need of such treatment, thereby treating the prostate cancer or breast cancer, wherein the compound is of formula

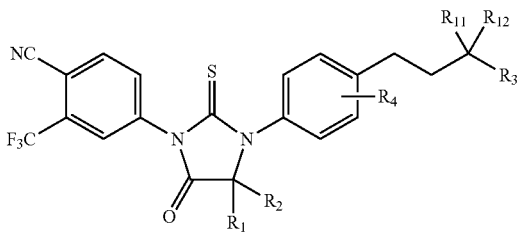

wherein R₁ and R₂ together comprise eight or fewer carbon atoms and are alkyl, or are substituted alkyl, or, together with the carbon to which they are linked, form a cycloalkyl or substituted cycloalkyl group, wherein R₄ is selected from the group consisting of hydrogen, F, Cl, Br, and I, wherein R₁₁ and R₁₂ are independently selected from the group consisting of hydrogen and methyl, wherein R₃ is selected from the group consisting of formyl,

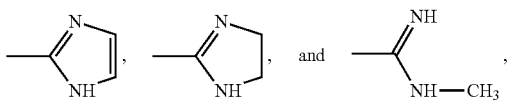

provided that when R₄, R₁₁, and R₁₂ are all hydrogen and when R₁ and R₂ together with the carbon to which they are linked are cyclobutyl, then R₃ is not formyl, or a pharmaceutically acceptable salt thereof.

2. The method of claim 1, wherein R3 of the compound is selected from the group consisting of

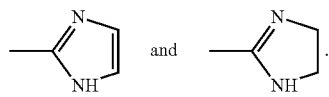

3. The method of claim 1, wherein the compound is of formula

wherein R21 is selected from the group consisting of

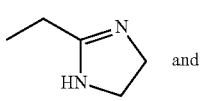

[ND-11]

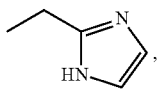

[ND-12]

or a pharmaceutically acceptable salt thereof.

4. The method of claim 1, wherein the compound is administered as a pharmaceutical composition comprising the compound and a pharmaceutically acceptable carrier or diluent.

5. The method of claim 1, wherein the compound is administered at a dosage of the compound in the range of from about 0.001 mg per kg body weight per day to about 100 mg per kg body weight per day.

6. The method of claim 1, wherein the compound is administered at a dosage of the compound in the range of from about 0.01 mg per kg body weight per day to about 100 mg per kg body weight per day.

7. The method of claim 1, wherein the compound is administered at a dosage of the compound in the range of from about 0.1 mg per kg body weight per day to about 10 mg per kg body weight per day.

8. The method of claim 1, wherein the compound is administered at a dosage of the compound of about 1 mg per kg body weight per day.

9. The method of claim 1, for treating hormone refractory prostate cancer.

10. The method of claim 1, wherein the compound is administered by intravenous injection, by injection into tissue, intraperitoneally, orally, or nasally.

11. The method of claim 1, wherein the compound is administered orally.

12. The method of claim 4, wherein the pharmaceutical composition has a form selected from the group consisting of a solution, dispersion, suspension, powder, capsule, tablet, pill, time release capsule, time release tablet, and time release pill.

13. The method of claim 4, wherein the pharmaceutical composition has a form selected from the group consisting of a capsule, tablet, and pill.

14. The method of claim 1, wherein the compound is of formula

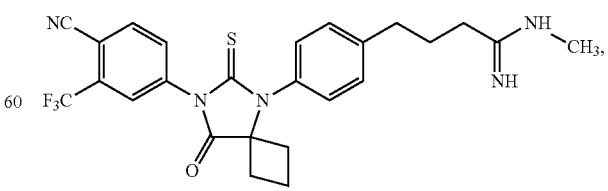

ND-3 or a pharmaceutically acceptable salt thereof.

15. The method of claim 1, wherein the compound is of formula

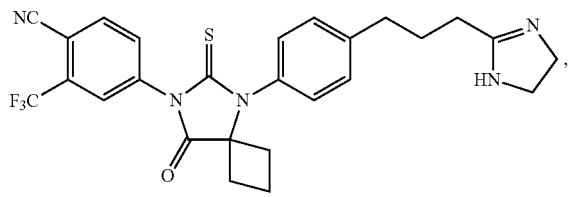

ND-11 or
a pharmaceutically acceptable salt thereof.

16. The method of claim 1, wherein the compound is of formula

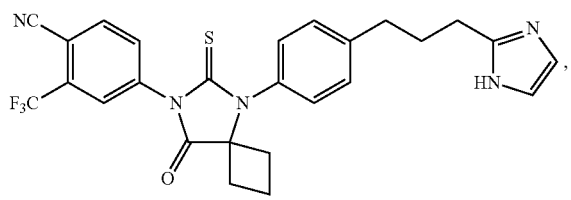

ND-12 or
a pharmaceutically acceptable salt thereof.

17. The method of claim 1, for treating hormone sensitive prostate cancer.

18. The method of claim 1, for treating breast cancer.

19. The method of claim 9, wherein the compound is of formula

ND-3 or
a pharmaceutically acceptable salt thereof.

20. The method of claim 9, wherein the compound is of formula

ND-11 or
a pharmaceutically acceptable salt thereof.

21. The method of claim 9, wherein the compound is of formula

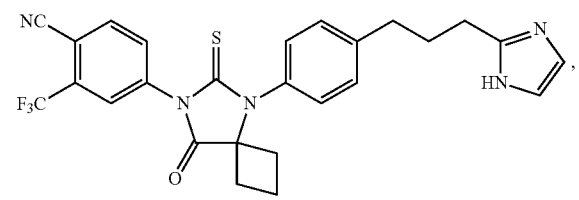

ND-12 or
a pharmaceutically acceptable salt thereof.

* * * * *